(12) United States Patent
Brungart et al.

(10) Patent No.: US 10,681,475 B2
(45) Date of Patent: Jun. 9, 2020

(54) SYSTEM AND METHOD FOR EVALUATING SPEECH PERCEPTION IN COMPLEX LISTENING ENVIRONMENTS

(71) Applicants: The Unites States of America Represented by the Secretary of Defense, Silver Spring, MD (US); The United States of America as Represented by the Secretary of the Army, Silver Spring, MD (US)

(72) Inventors: Douglas S. Brungart, Rockville, MD (US); Benjamin M Sheffield, San Luis Obispo, CA (US)

(73) Assignee: The United States of America as Represented by the Secretary of Defense, Bethesda, MD (US)

( * ) Notice: Subject to any disclaimer, the term of this patent is extended or adjusted under 35 U.S.C. 154(b) by 0 days.

(21) Appl. No.: 16/279,675

(22) Filed: Feb. 19, 2019

(65) Prior Publication Data
US 2019/0261095 A1 Aug. 22, 2019

Related U.S. Application Data

(60) Provisional application No. 62/631,700, filed on Feb. 17, 2018.

(51) Int. Cl.
| | |
|---|---|
| H04R 29/00 | (2006.01) |
| H04R 25/00 | (2006.01) |
| G10L 21/0208 | (2013.01) |
| H04R 3/04 | (2006.01) |
| H04S 7/00 | (2006.01) |
| G10L 25/48 | (2013.01) |
| A61B 5/12 | (2006.01) |

(52) U.S. Cl.
CPC .......... *H04R 25/30* (2013.01); *G10L 21/0208* (2013.01); *G10L 25/48* (2013.01); *H04R 3/04* (2013.01); *H04S 7/303* (2013.01); *A61B 5/12* (2013.01); *G10L 2021/02082* (2013.01); *H04R 2225/31* (2013.01); *H04S 2420/01* (2013.01)

(58) Field of Classification Search
CPC ...... H04R 3/04; H04R 25/30; H04R 2225/31; H04R 2225/33; H04R 2225/39; H04R 2225/43; G10L 21/0208; G10L 21/02082; G10L 25/48; G10L 25/60; G10L 15/20; A61B 5/12; G10K 11/175
USPC .............................. 381/60, 72, 73.1, 63, 110
See application file for complete search history.

(56) References Cited

U.S. PATENT DOCUMENTS

| | | | | |
|---|---|---|---|---|
| 6,167,138 A | * | 12/2000 | Shennib | G16H 40/40 381/60 |
| 8,812,014 B2 | * | 8/2014 | Do | G01S 5/18 455/456.1 |

(Continued)

*Primary Examiner* — Xu Mei
(74) *Attorney, Agent, or Firm* — Albert M Churilla; Ning Yang; Diane Tso

(57) ABSTRACT

The present application describes a plurality of test simulation environment mimic complex listening environment of everyday life, comprising a speech component, and a noise component. The application also describes an auditory testing system and method for evaluating a listener's speech perception and method to test hearing prosthesis or hearing protection device's effect on a person's speech perception in a complex listening environment.

11 Claims, 14 Drawing Sheets

(56) References Cited

U.S. PATENT DOCUMENTS

| | | | | |
|---|---|---|---|---|
| 9,031,242 B2 * | 5/2015 | Edwards | .............. | H04R 25/552 |
| | | | | 381/17 |
| 9,833,174 B2 * | 12/2017 | Bochner | ................ | A61B 5/123 |
| 10,536,775 B1 * | 1/2020 | Sen | ........................ | H04R 3/005 |
| 2010/0246837 A1 * | 9/2010 | Krause | .................. | G10L 15/063 |
| | | | | 381/58 |
| 2013/0259237 A1 * | 10/2013 | Oesch | .................. | H04R 25/407 |
| | | | | 381/2 |

\* cited by examiner

SYSTEM AND METHOD FOR EVALUATING SPEECH PERCEPTION IN COMPLEX LISTENING ENVIRONMENTS

CROSS-REFERENCE TO RELATED APPLICATION

This application claims the benefit of priority from, and hereby incorporates by reference, U.S. Provisional Patent Application No. 62/631,700 filed on Feb. 17, 2018.

STATEMENT REGARDING FEDERALLY SPONSORED RESEARCH OR DEVELOPMENT

This invention was made with United States government support awarded by DMRDP Grant D61-I-10-J8-261.

BACKGROUND

Technical Field

The present technology pertains generally to a method and system for evaluating a person's speech perception in complex listening environments, and more particularly to a system and method to evaluate speech perception using auditory stimuli that mimic real listening conditions spanning the range of auditory environments listeners would encounter in everyday life.

Background

Good hearing is essential to our ability to socialize, communication and work. A normal-hearing listener can communicate even in very complex listening scenarios using various auditory skills and processes, including the ability to segregate the sound of interest from the interfering noise, attending to one out of multiple simultaneous audio signals, modulation masking release, spatial release from masking etc. (Freyman et al., 2001; Dubno et al., 2002; Buss et al., 2009; Litovsky, 2012). These auditory skills are known to degrade with increasing hearing loss.

Hearing difficulties due to hearing loss are often first apparent in difficult listening environments that involve noisy reverberant spaces, multi-talker conversations, rapid speaking rates, and other complicating factors that are typically not present in the clinical spaces or in the standardized tests used to assess hearing loss (Pienkowski, 2016). This may help explain why clinical assessments of hearing loss often do not correlate with the everyday speech-in-noise communication difficulties reported by patients (Hannula et al., 2011; Jerger, 2011).

One shortcoming of existing clinical speech-in-noise tests is that they tend to be focused on relatively simple listening situations that do not fully reflect the complex listening environments that hearing impaired listeners experience in the real world. Clinical speech-in-noise tests are generally presented diotically with clearly and carefully articulated speech signals presented in stable and predictable noise backgrounds. They do not contain the binaural cues that typically occur in real world auditory stimuli where target and masking sounds almost always originate from different spatial locations. Clinical speech-in-noise test materials are also almost always presented anechoically. This means that they lack the signal distortions that occur due to room reverberation in the kinds of indoor listening environments where most voice communication occurs. Finally, clinical speech-in-noise stimuli are almost always presented without visual speech cues, which are available to most hearing impaired listeners when they attempt to communicate in high-noise environments.

The inability of current clinical speech-in-noise tests to capture the complexities of real-world speech communication is a significant problem in the assessment and treatment of hearing loss. Virtually all practitioners of clinical audiology have encountered patients who perform acceptably in clinical testing, but report that they have substantial difficulty understanding speech in real world environments like bars and restaurants. The ability to clinically assess speech perception in a variety of environments that more realistically represent real world listening situations would make it much easier for audiologists to determine whether listeners who complain about speech perception problems in complex environments are truly performing much worse than normal hearing listeners in these environments. Identifying speech perception problems would also make it easier for clinicians to develop treatment strategies and to assess the effectiveness of these strategies.

To overcome these problems, Brungart et al. (2014) altered the a single noise stimulation condition and testing paradigm of the QuickSIN test (Killion et al, 2004) to develop a short clinical test for measuring speech reception thresholds (SRTs) in seven additional auditory scenes (simuli conditions), and evaluated its efficacy on 49 normal-hearing listeners against the standard QuickSIN test.

While some listening conditions were expected to be easier for speech communication than the standard QuickSIN condition due to the ability of a normal-hearing listener to benefit from the binaural release from masking, and from integrating audio and visual speech cues, hearing loss can potentially degrade these abilities, resulting in worse-than-normal performance in these conditions. On the other hand, some listening conditions were expected to be more difficult than the standard condition. These particular conditions were designed to simulate challenging acoustic environments such as reverberant rooms, continuous noise, and fast talkers, where people with even mild to moderate hearing loss often complain of communication difficulties (Gordon-Salant & Fitzgibbons, 1993). When combined with the standard QuickSIN condition, test simulation environments of this invention can provide a more circumscribing assessment of a person's operational speech communication ability. For occupations such as firefighting, aviation, law enforcement, military etc., where communication is critical for mission success and survivability, such an assessment can be potentially used for predicting fitness-for-duty. This test battery is also useful for studying the effect of a hearing prosthesis or a hearing protection device on everyday speech communication.

While the 2014 Brungart test results are encouraging. The mean SRT50 and test-retest reliability scores that were comparable to those obtained in other studies that have evaluated performance for QuickSIN stimuli in a population of normal-hearing listeners. The test-retest reliability of the SRT50 values measured with the modified QuickSIN listening conditions was also comparable to that obtained with the baseline four-talker babble QuickSIN condition. The differences in mean performance across the eight listening conditions suggested that there are meaningful differences across the listening conditions tested in this experiment and that it is possible to measure these differences with the modified QuickSIN stimuli presented here.

However, without validating modified QuickSIN listening (simulation) conditions on hearing impaired individuals, it is not clear whether the simuli conditions would be effective in detecting speech perception impairment of a listener. It is also unclear if any of the seven additional simuli conditions is more sensitive for speech perception. Additional modifications are also required (1) to set the SNR values tested to a fixed range rather than the adaptive range (based on the method of adjustment measures) used here, and (2) to make adjustments to account for any differences in difficulty across the 16 lists used in the experiment. These issues were examined in follow-up research involving normal and hearing impaired listeners (Brungart 2018), which provided validation for the present invention.

The present invention describes a system and an extended battery of speech-in-noise tests that would allow clinicians and researchers to assess the functional hearing performance of listeners in a variety of different listening environments that attempt to capture the range of different kinds of auditory distortions and speech segregation cues listeners are likely to encounter in real-world listening. The present invention is also directed to methods for evaluating a listener's speech perception performance or the effectiveness of a hearing prosthesis or a hearing protection device for a listener in a variety of different listening environments.

DETAILED DESCRIPTION OF FIGURES

Figure 2:
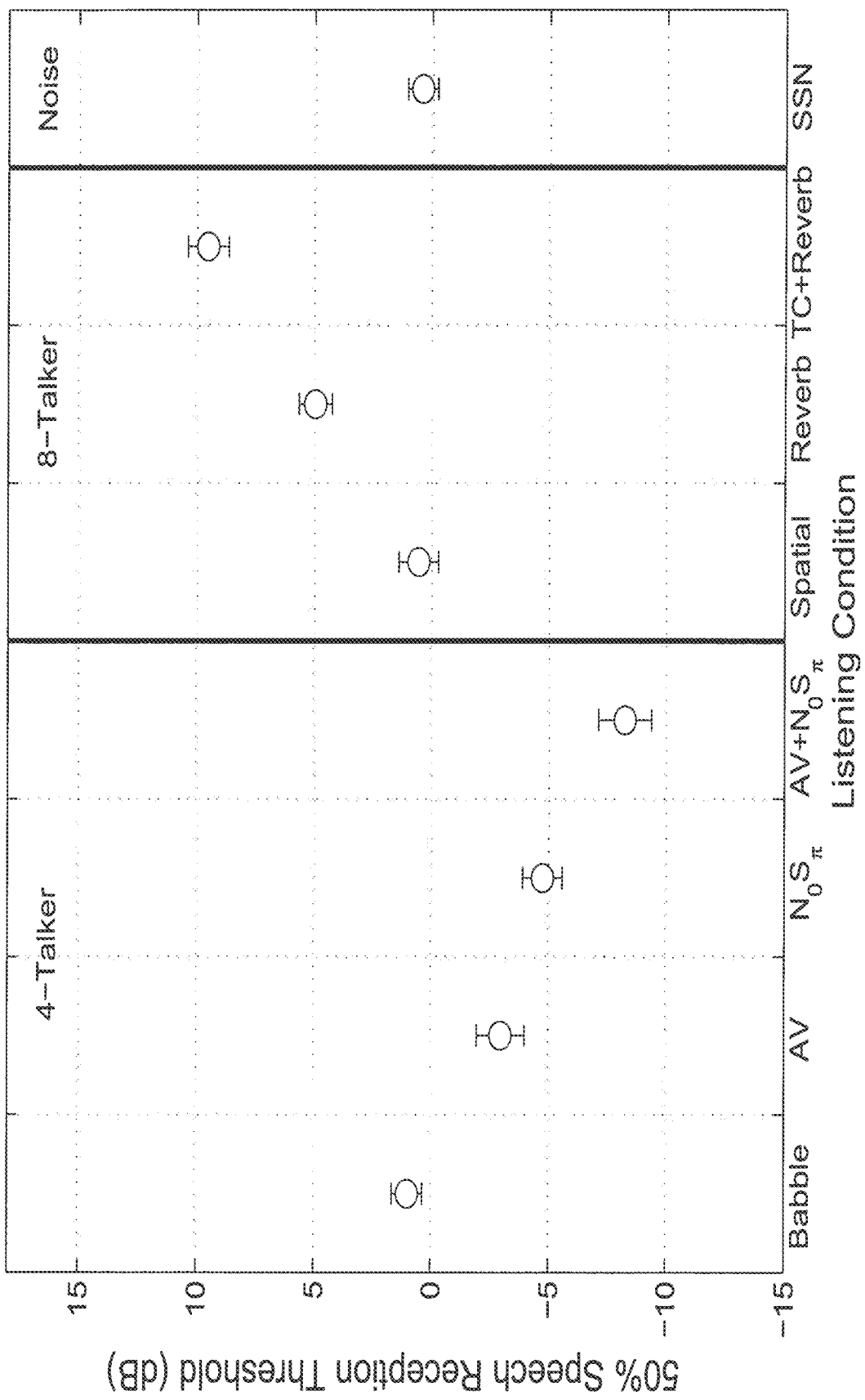

FIG. 2. Mean SRT50 values for each listening condition tested in the experiment. The error bars show the 95% confidence intervals in the standard errors calculated across the 49 normal hearing listeners in the experiment.

Figure 3:
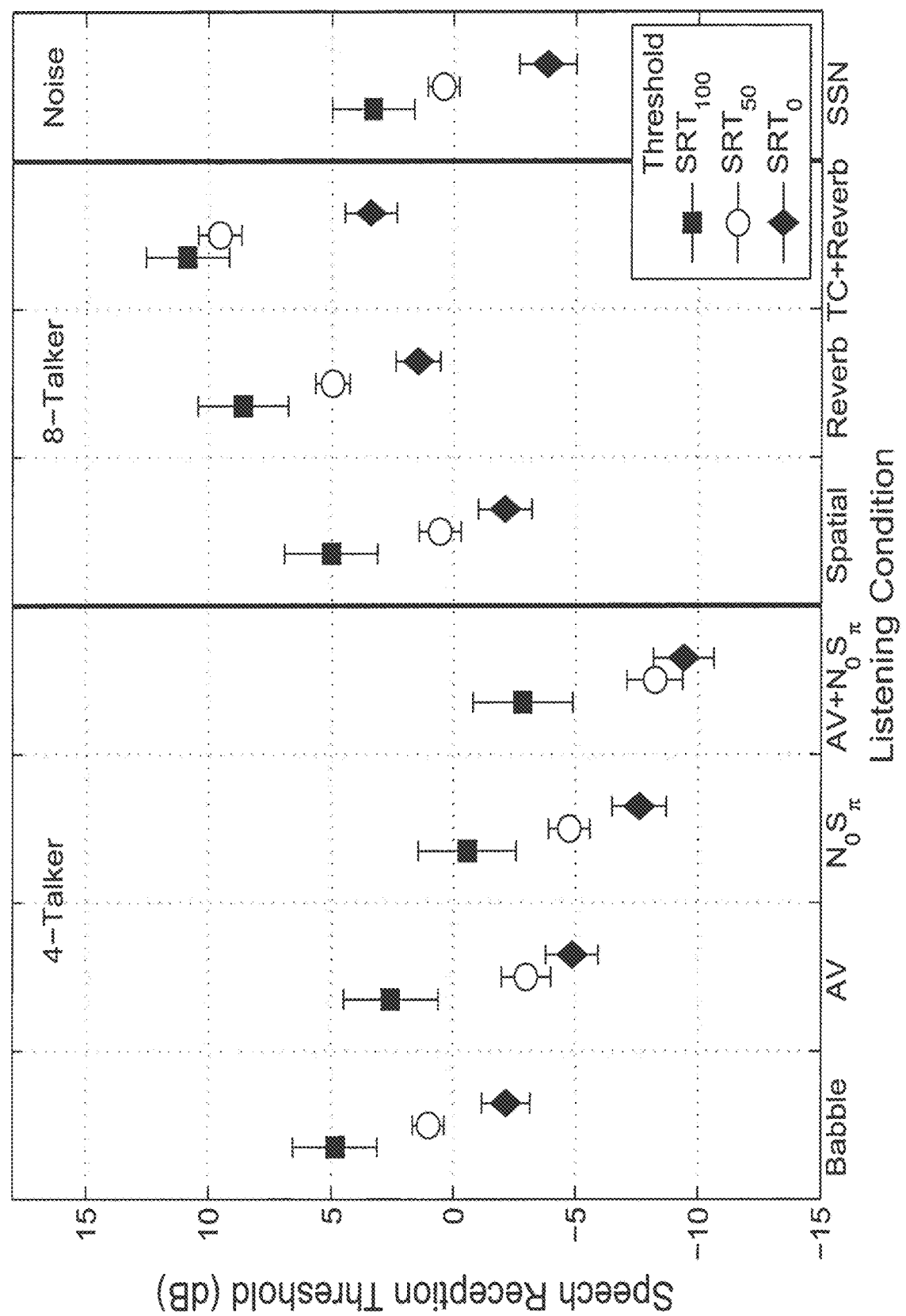

FIG. 3 (Color online) Mean values for each listening condition and SRT value tested in the experiment. The error bars show the 95% confidence intervals in the standard errors calculated across the 49 normal hearing listeners in the experiment. Note that a two factor repeated measures ANOVA on the main factors of listening condition and SRT type showed that both of these factors and their interaction were significant at the $P<0.001$ level.

Figure 4:
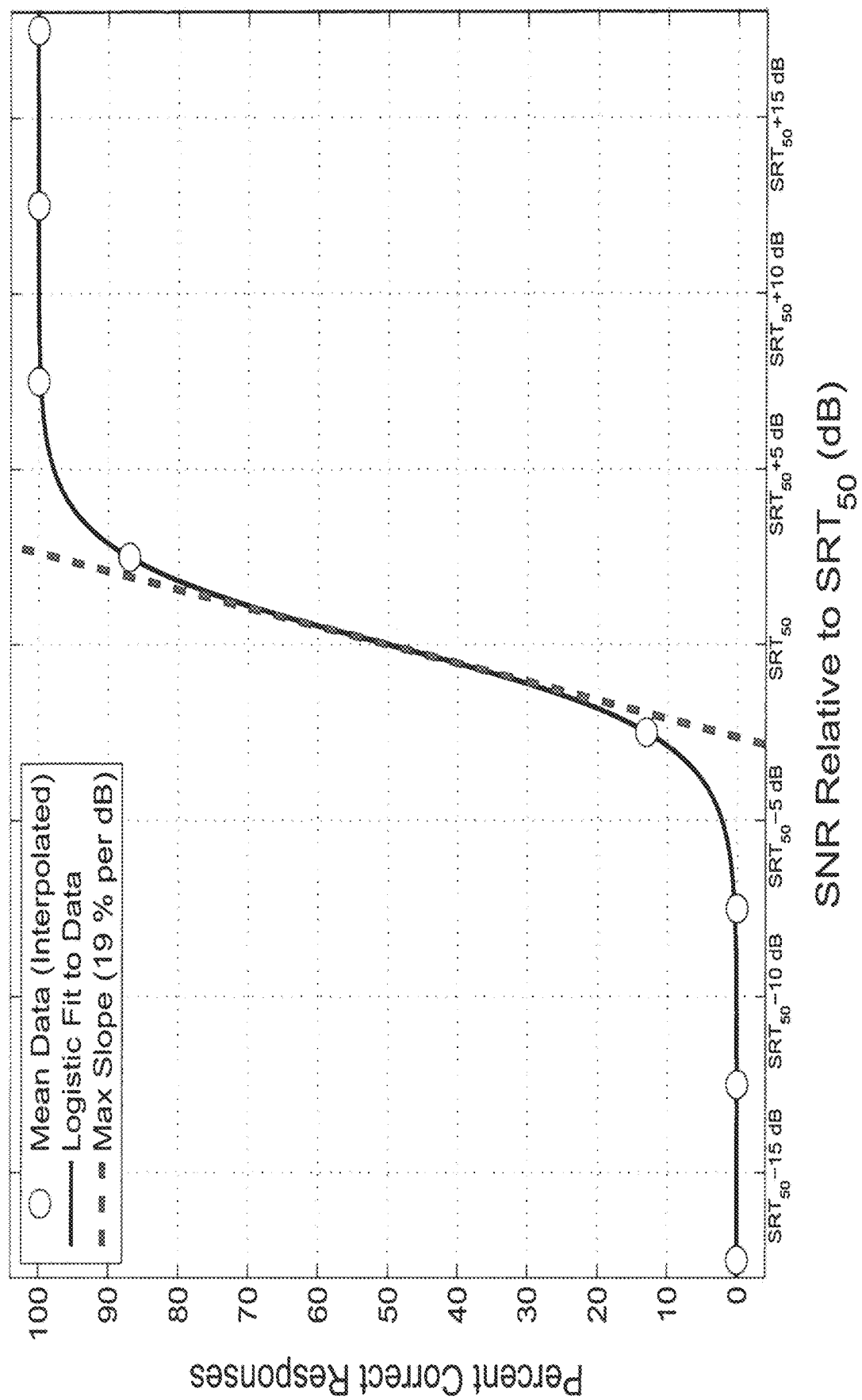

FIG. 4. (Color online) Calculation of slope from data for a single normal hearing subject in the standard four-talker babble condition of the experiment. The slopes for each subject in each condition were estimated from the maximum slope of a logistic curve fitting the mean data estimated for SNR values ranging from −12.5 to 12.5 dB around the SRT50 value calculated for each list using the Tillman-Olsen procedure. Note that this procedure aligns the psychometric curves in cases where the SRT50 estimate differed across the two lists collected in the same condition with the same subject.

Figure 5:
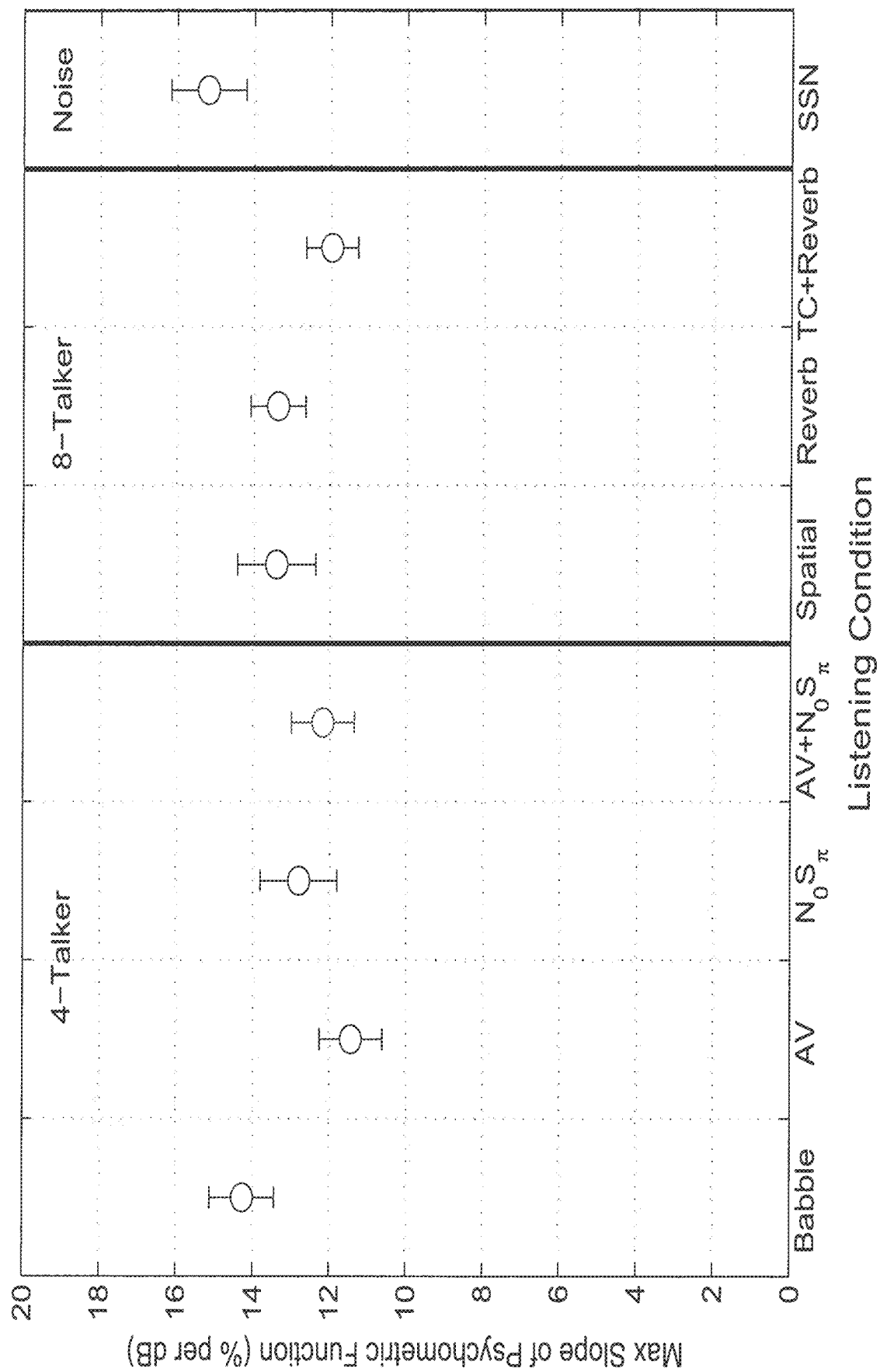

FIG. 5 Mean slope estimates for each listening condition for the normal hearing listeners tested in the experiment. The error bars show 61 standard error around each condition.

Figure 6:
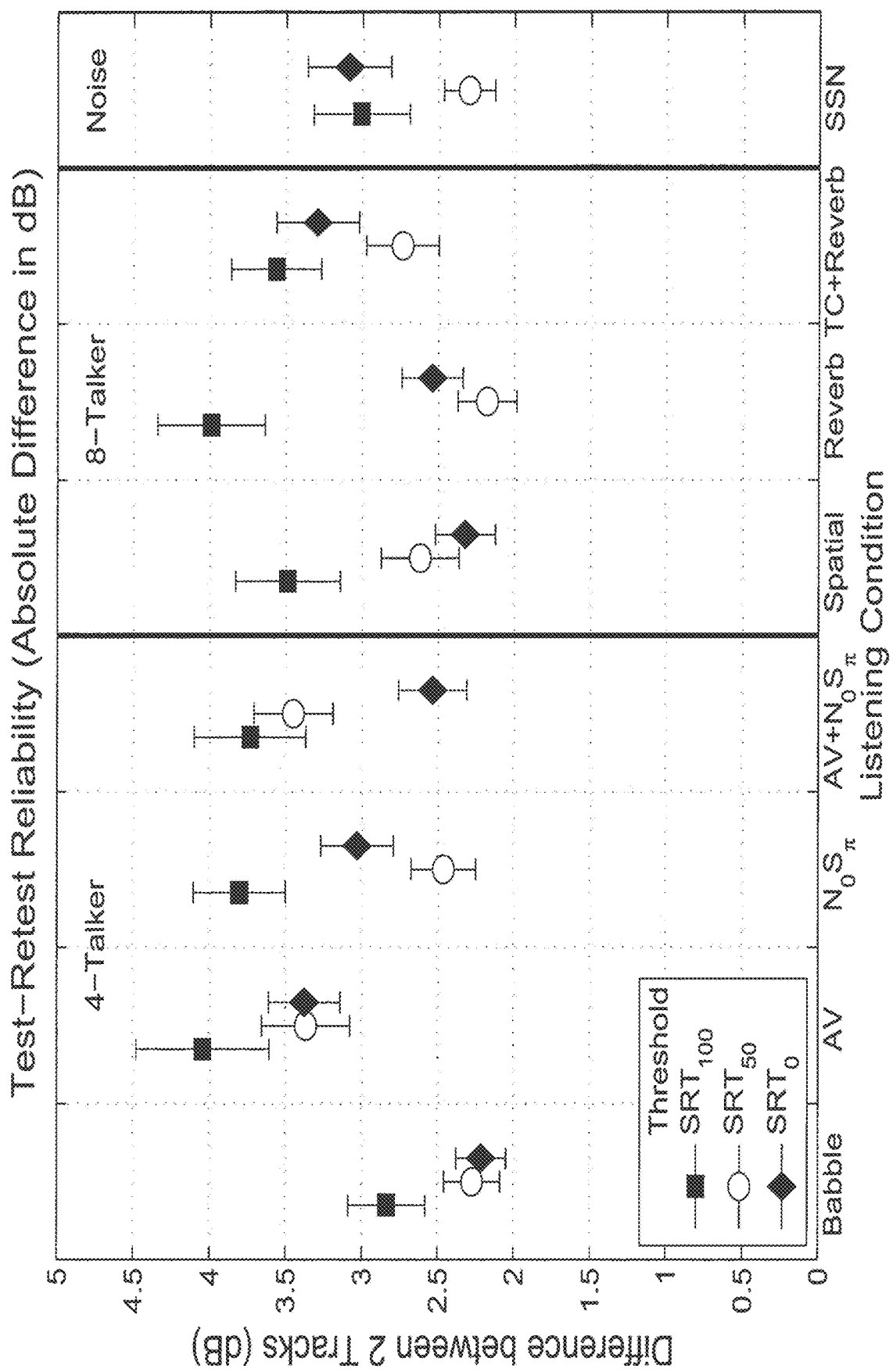

FIG. 6 (Color online) Test-retest reliability in each condition is shown by the mean absolute difference between the two SRT estimates of each type made in each condition by each listener.

Figure 7:
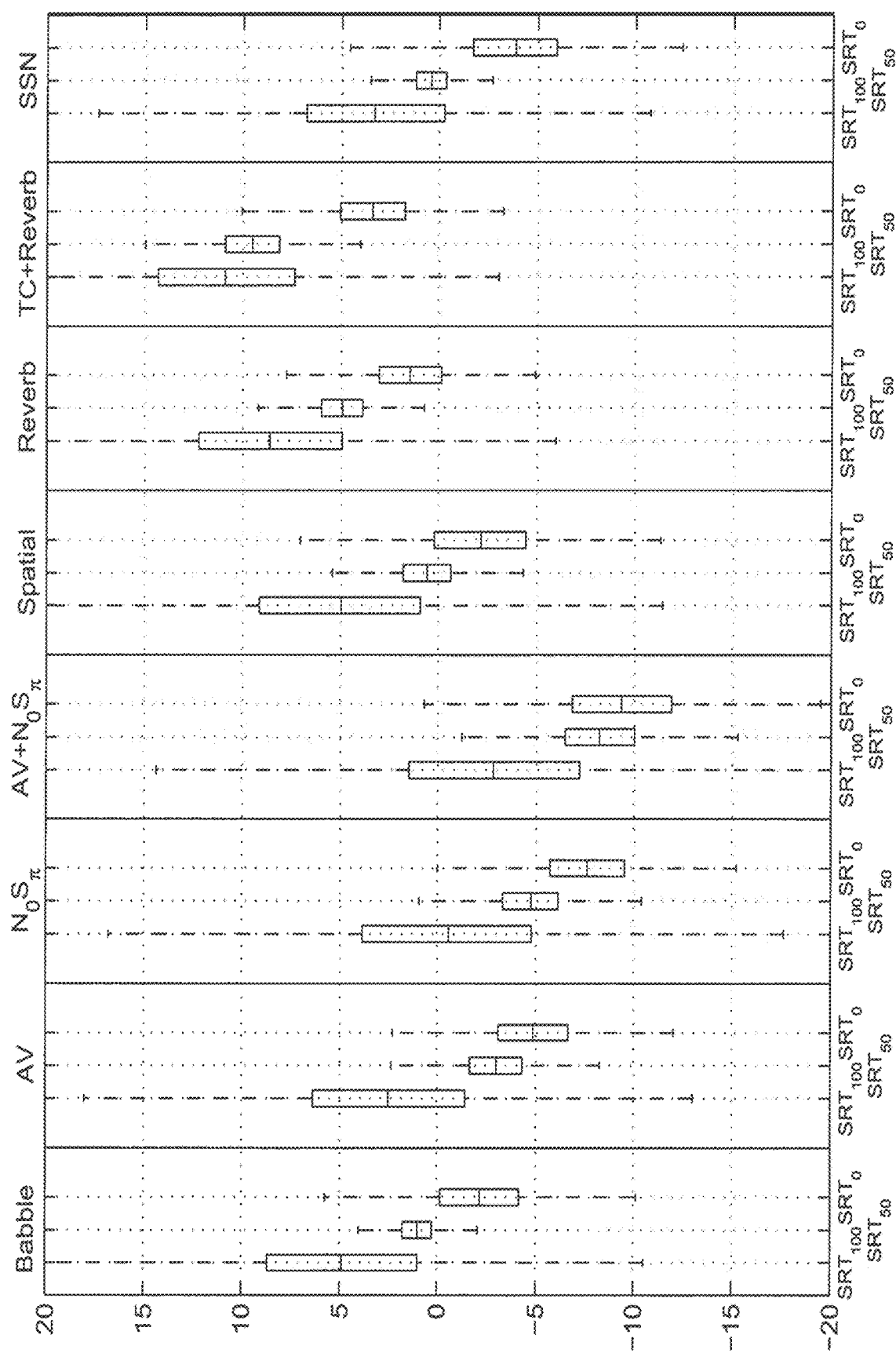

FIG. 7 (Color online) Box plots showing estimates of distributions of SRT values in the overall population of listeners with normal hearing. The boxes at the middle of each line show the estimated 25th, 50th, and 75th percentiles for each condition, while the whiskers show the 5th and $95^{th}$ percentiles.

Figure 8:
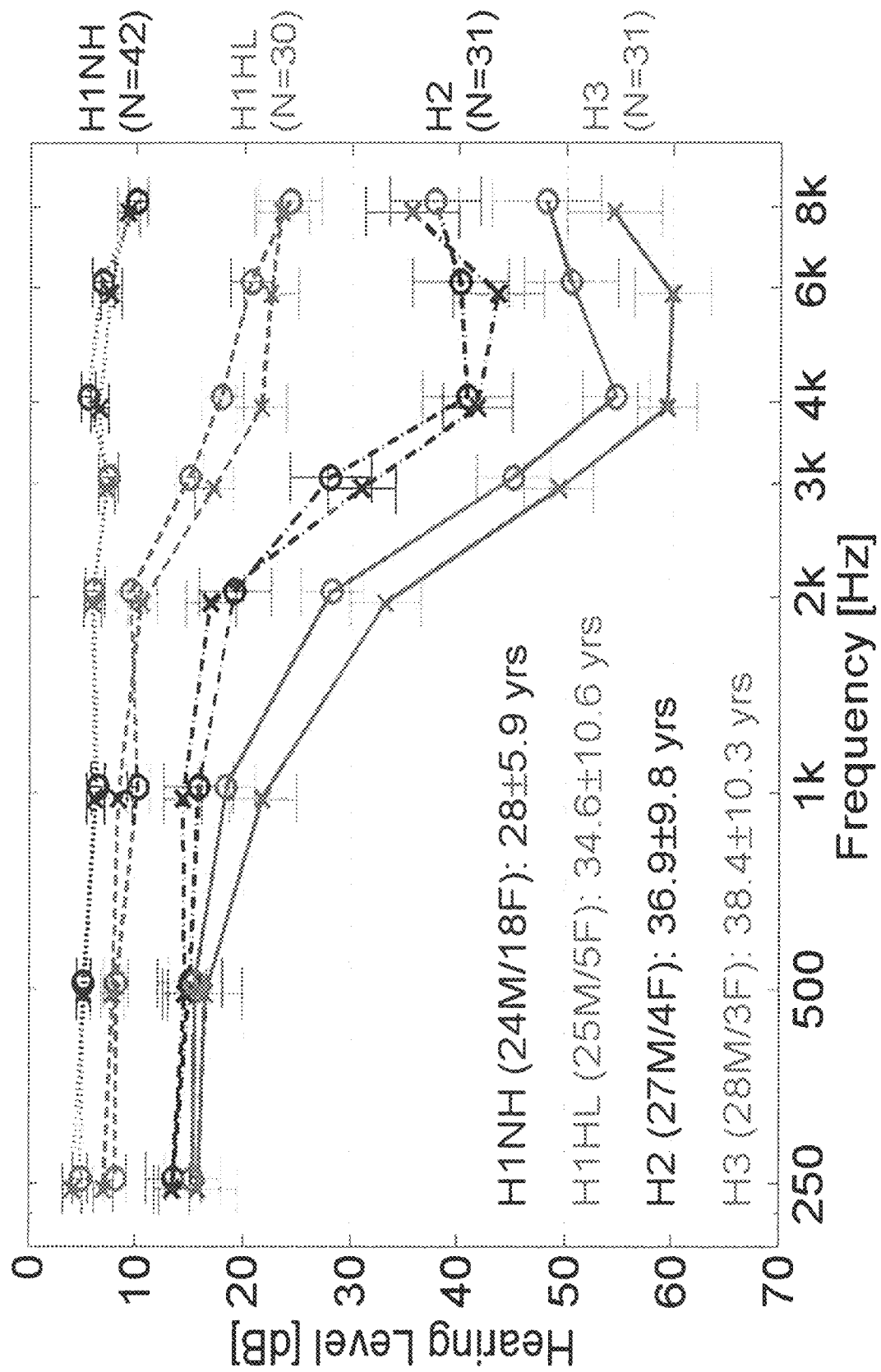

FIG. 8 Average audiometric thresholds in left (x) and right (o) ears for the four listener groups. Symbols and errorbars represent means and ±1 standard errors across listeners within each group. Number of male (M) and female (F) participants in each group, and the mean and ±1 standard deviation of participant age in each group are also listed.

Figure 9:
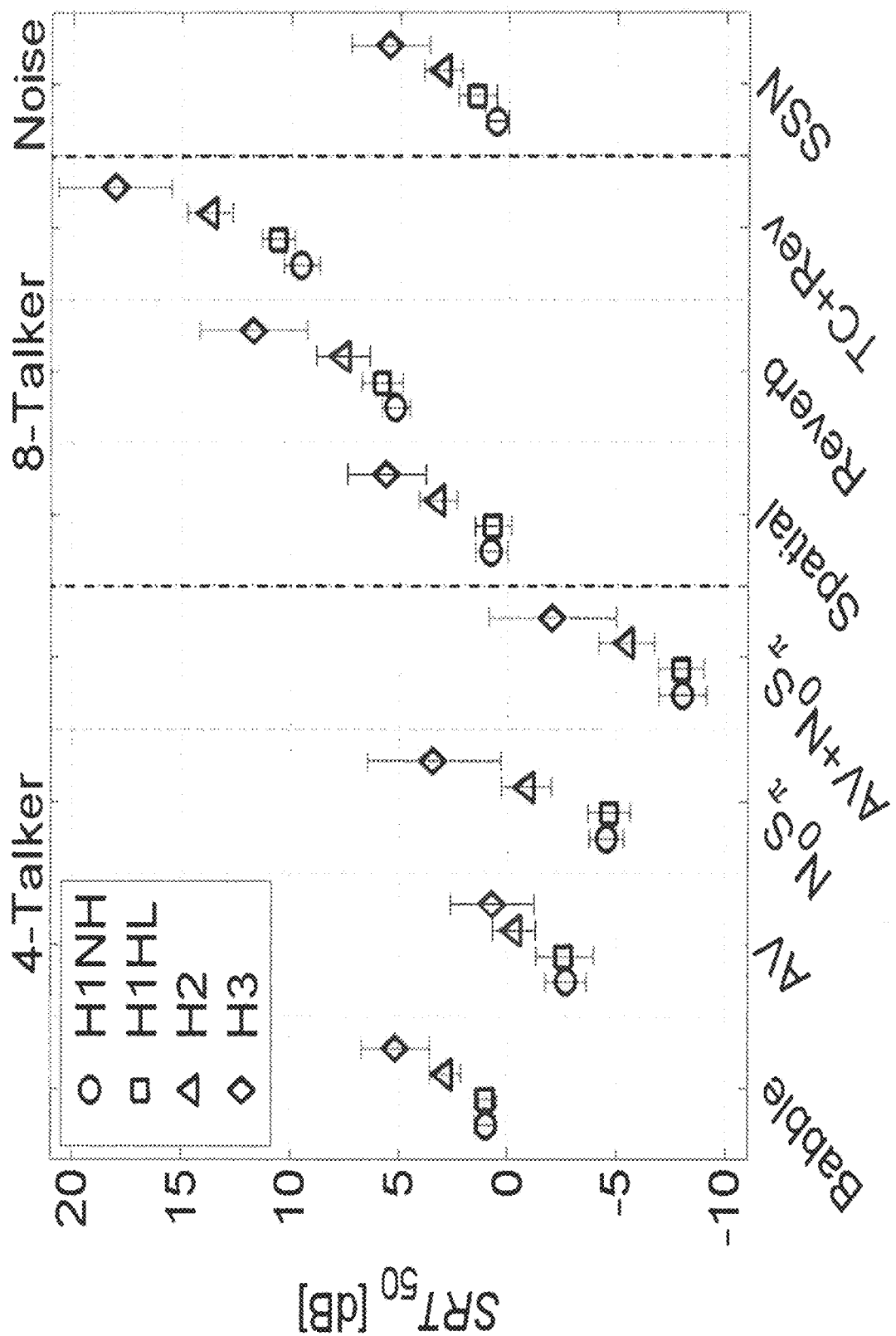

FIG. 9 Measured speech-in-noise thresholds ($SRT_{50}$) for each group in all eight listening conditions. Symbols and errorbars denote means and 95% confidence intervals estimated across listeners within each group.

Figure 10:
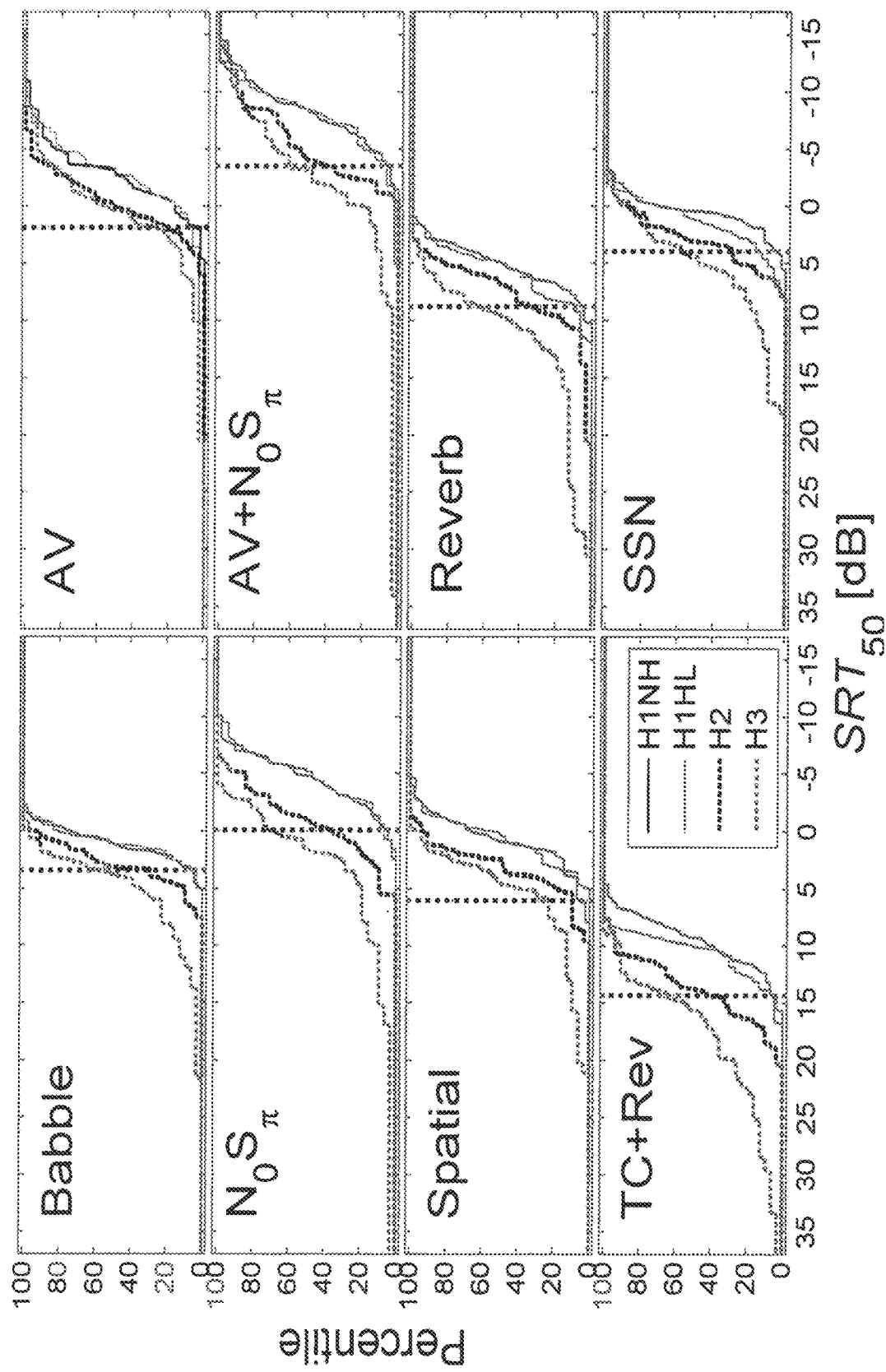

FIG. 10 $SRT_{50}$ cumulative distributions (in percentile). The vertical dash-dotted line in each panel represents the $5_{th}$ percentile value for H1NH group in each condition.

Figure 11:
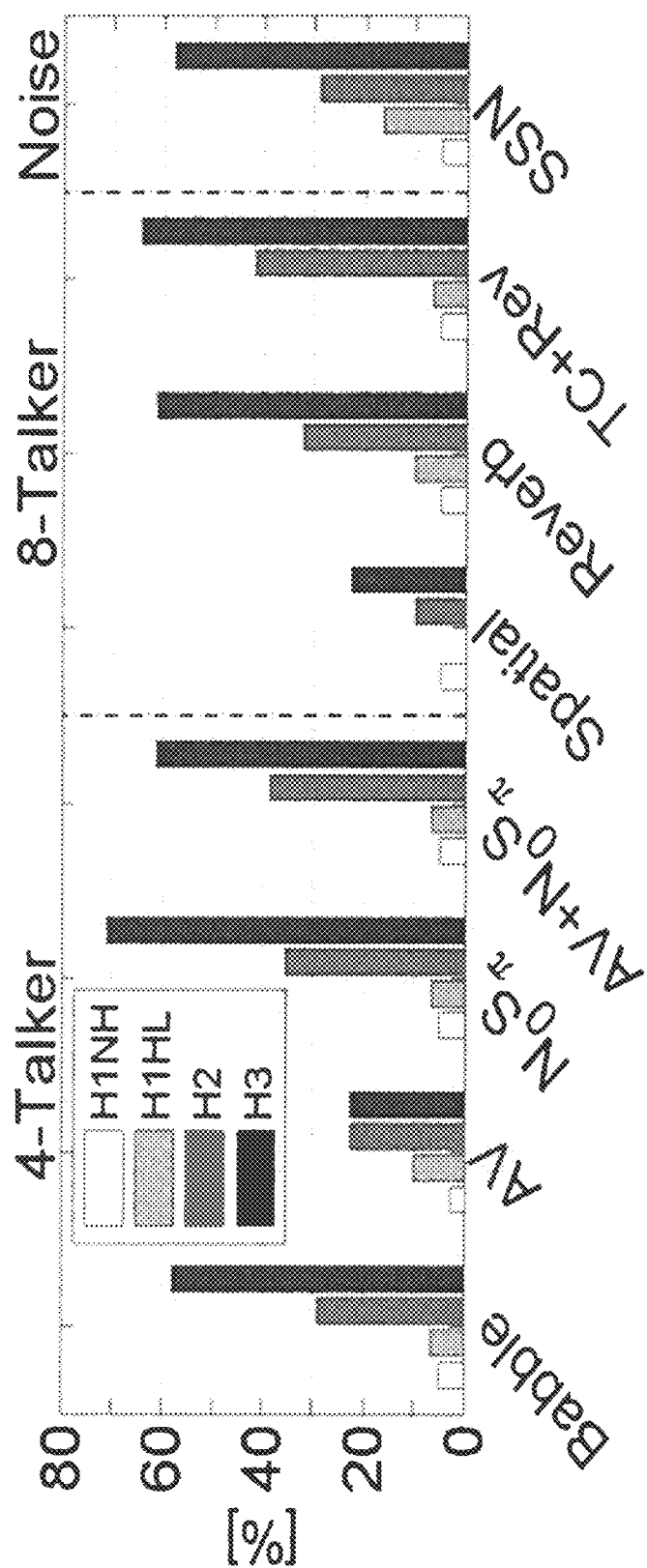

FIG. 11 The percentage of participants in each group having an $SRT_{50}$ higher (i.e., worse performance) than the $5_{th}$ percentile value for the control group in each listening condition.

Figure 12:
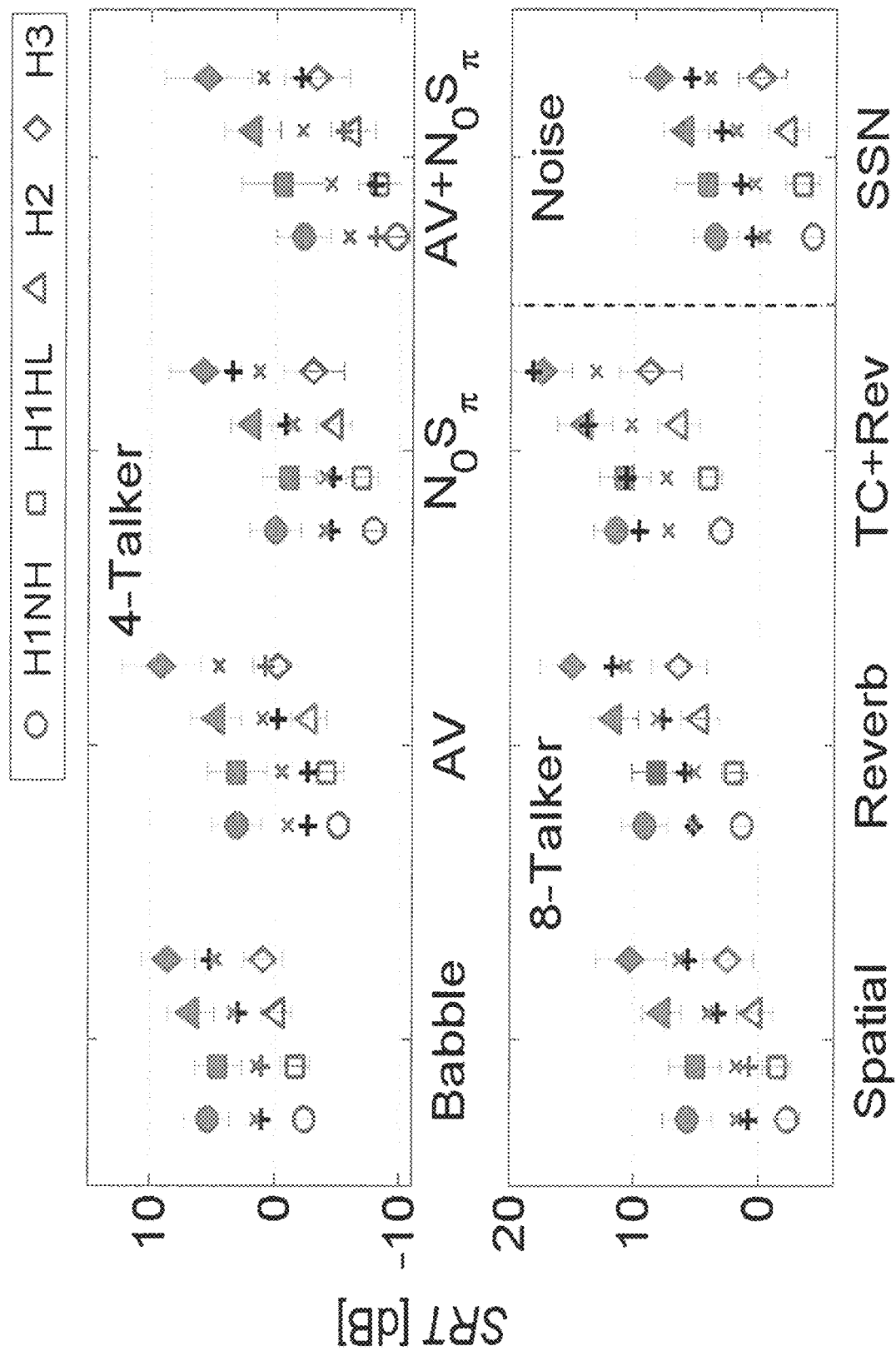

FIG. 12 Subjectively estimated speech-in-noise thresholds $SRT_0$ (open symbols) and $SRT_{100}$ (filled symbols) for each group in all eight listening conditions. Symbols and errorbars denote means and 95% confidence intervals estimated across listeners within each group. In each case, the grey x symbol denotes the mid-way point between $SRT_0$ and $SRT_{00}$, whereas the black + symbol represents the average $SRT_{50}$ value.

Figure 13:
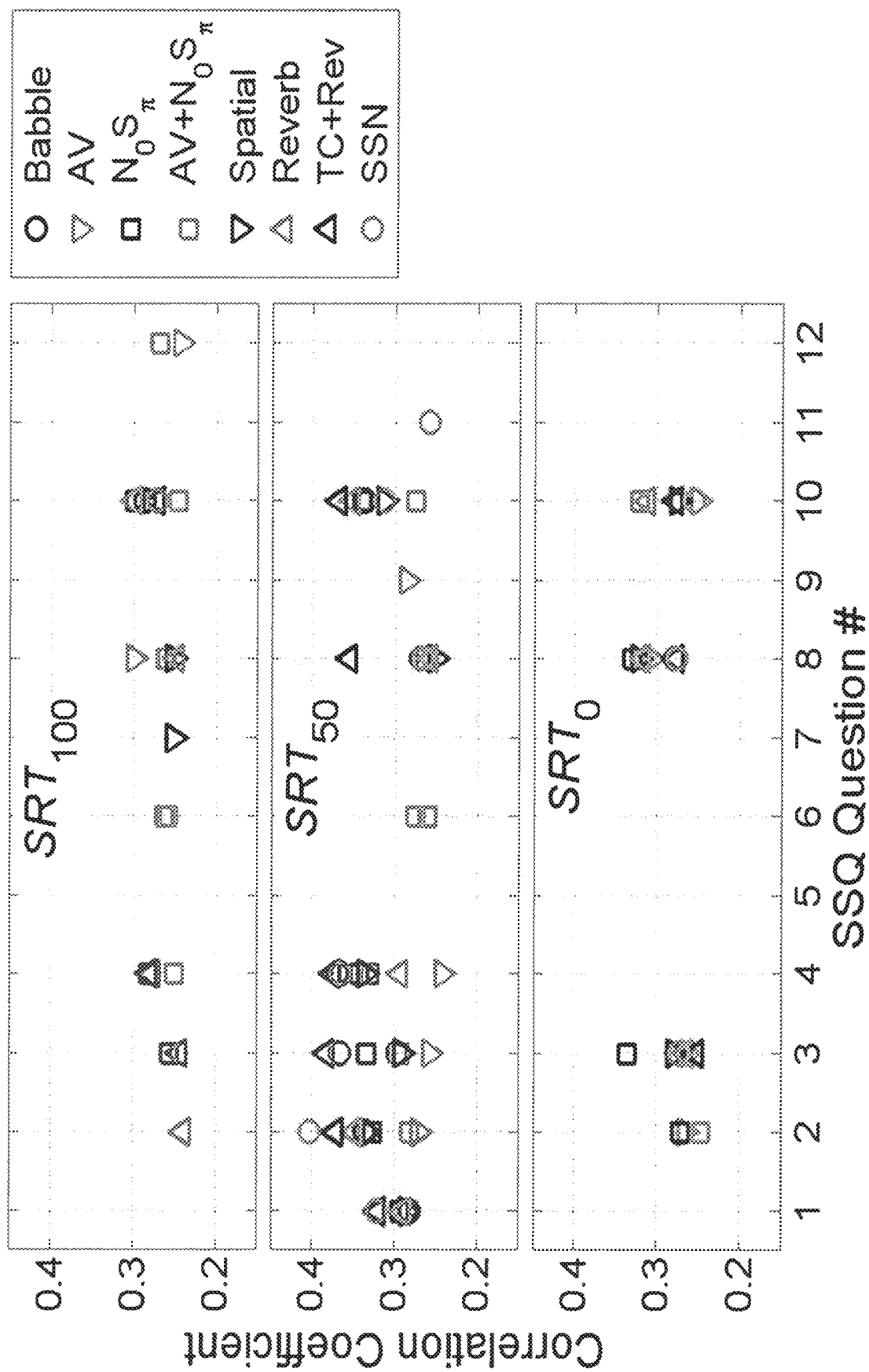

FIG. 13 Pearson correlation coefficient magnitudes between ratings on the twelve SSQ questions and subjective ($SRT_0$, $SRT_{00}$) and measured thresholds ($SRT_{50}$) in the eight listening conditions. Only those correlations that were statistically significant after Bonferroni correction are plotted. Correlation coefficients were positive for questions 8 and 10, and negative for the remaining questions.

SUMMARY OF INVENTION

One aspect of the technology is to provide an expanded speech-in noise test to simulate a plurality of test stimulus conditions mimicking complex listening environments of everyday life. Each stimulation conditions comprises a speech component (signal) and a noise component (signal).

A further aspect of the technology is to provide an auditory testing system for evaluating performance of speech perception of a listener.

Another aspect of the technology is to provide a method to identify patients with speech-in-noise deficits.

Another aspect of the technology is to provide a method for testing the effectiveness of a hearing prostheses or hearing protection devices for a listener in terms of speech perception.

Further objects and aspects of the technology will be brought out in the following portions of the specification, wherein the detailed description is for the purpose of fully disclosing preferred embodiments of the technology without placing limitations thereon.

DETAILED DESCRIPTION OF THE INVENTION

Definition

The following non-exhaustive list of definitions is used herein to define terms that may otherwise be confusing or can sometimes have multiple meanings. Each occurrence of a defined term in the above text, in the text that follows, or in the claims of this document, is to be given the meaning ascribed to it in the list of definitions below.

"Noise Masker or Masking Noise" as referred to in this document is a noise or speech waveform added to a speech signal to make it more difficult to understand.

"Babble" as referred to in this document is a mixture of two or more talkers at the same overall root-mean-square level speaking continuous speech.

"signal to noise ratio" as referred to in this document is the difference in dB between the root-mean-square level of the target signal and the root-mean-square level of all the interfering noise waveforms present in the stimulus.

"diotically" as referred to in this document is involving the simultaneous presentation of the same stimulus to each ear; (also) designating such a stimulus. Also more generally: using both ears; binaural.

"monaural" as referred to in this document refers to signals presented to only one ear.

"binaural" as referred to in this document is refers to signals presented to both ears with the natural interaural time and intensity differences that would occur for spatially separated speech and noise signals in a room in the real world.

"continuous speech-spectrum shaped noise masker" as referred to in this document is a stationary noise that has been shaped to have the same long-term spectrum as the target speech signal.

"Reverberation" as refers to in this document is a prolongation of sound such as echo, vibration.

"test battery" as refers to in this documents is a series of audiovisual stimuli of a series of list of questions of similar difficulties and may be separated into a noise component and a speech component. The battery may be stored on computer readable medium or in a computer or audio testing device.

In the course of the detailed description to follow, reference will be made to the attached drawings. These drawings show different aspects of the present inventions and where appropriate, reference numerals illustrating like structures, components, materials and/or elements in different figures are labeled similarly. It is understood that various combinations of the structures, components, materials and/or elements, other than those specifically shown, are contemplated and are within the scope of the present inventions.

Moreover, there are many inventions described and illustrated herein. The present inventions are neither limited to any single aspect nor embodiment thereof, nor to any combinations and/or permutations of such aspects and/or embodiments. As will be appreciated by one skilled in the art, the present invention may be embodied as a system, method, or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "module" or "system." Furthermore, the present invention may take the form of a computer program product embodied in any tangible medium of expression having computer-usable program code embodied in the medium.

A. Development of the Modified Stimuli

A key aspect of the present invention is that it provides a means to take an existing speech and noise test that only consists of a single noise condition (typically diotic speech in diotic noise or monaural speech in monaural noise), and convert it into a battery of speech tests representing a full spectrum of listening conditions a hearing impaired listener might be likely to encounter in everyday life.

The following section describes how the method was used to derive multiple modified test stimuli from the QuickSIN test, a commercially available test that uses speech signals presented in four-talker babble to assess hearing impairment. A key component of the QuickSIN is that it is comprised of a series of lists of sentences where the speech signal and the noise signals have been adjusted to be roughly comparable across 12 lists of sentences. The QuickSIN stimuli are distributed in digital form on a Compact Disc (CD), where each track represents a different list of words and a separate track is available where the speech is presented on the left channel and the noise is presented on the right channel. Also, the actual speech stimuli in the Quick-SIN were originally recorded as an AudioVisual recording (a movie), so video versions of each sentence were available.

However, the inventive speech-in-noise test may be adapted from other commercial available test batteries that contain an audio or audiovisual tracks sentences of similar difficulties, of which the audio signal may be separated into a speech component and a noise component.

In the present embodiment of the invention, the QuickSIN stimuli were used to create a total of eight different listening conditions or test simulation environment:

Standard four-talker babble: This condition simply consisted of the standard QuickSIN stimuli in the same format provided on the original CD.

$N_0S_\pi$ or $N_0Spi$: Identical to the standard condition but with the phase of the target talker shifted 180° in the right ear. This condition was designed to evaluate the extent to which each listener was able to take advantage of the binaural masking level difference (BMLD) that occurs when there are differences in the interaural phase characteristics of a target and masking signal (Levitt and Rabiner, 1967). Although stimuli with binaural phase disparities of 180° across all frequencies are rarely encountered in real-world listening, the $N_0S_\pi$ condition produces the largest possible BMLD and thus should be maximally sensitive to the problems experienced by listeners who are unable to benefit from the interarual phase difference cues that occur in real-world sounds Audiovisual (AV): Identical to the standard condition but with a video signal of the target talker presented on an LCD monitor in the listener's booth. These video signals were derived from the original AV recordings from which the QuickSIN target audio was sourced at the Research Laboratory for Electronics at the Massachusetts Institute of Technology. These video files were time-aligned with the QuickSIN auditory stimuli by conducting a cross-correlation between the audio track of the video file and the target-only portion of the QuickSIN audio stimulus. The QuickSIN audio stimulus (containing a mixture of target and masker) was then redubbed onto the video file to create an AVI movie file.

AV+$N_0S_\pi$: Identical to the AV stimuli but with the same audio stimulus used in the $N_0S_\pi$ condition.

Spatial: In the standard spatial condition, head-related transfer functions (HRTFs) from the Knowles Acoustic Manikin for Auditory Research (KEMAR) were used to simulate a spatial condition with the target talker in front, a four-talker babble masker 90° to the left of the listener, and a second four-talker babble masker 90° to the right of the listener, each at a distance of 5 ft. These HRTFs were implemented using the MATLAB® RoomSIM function (Campbell et al., 2005) with the room characteristics set to replicate an anechoic environment. The maskers were selected to try to replicate the properties of the masking stimuli used in the original QuickSIN as closely as possible. Thus in all cases, the masker on the left side was taken from the original four-talker babble on the same track as the target phrase, and the masker on the right side was selected from the masker that was paired with a different target phrase on the original CD.

Reverb: the reverb condition was identical to the spatial condition except that the room characteristics were changed to simulate the room reverberation characteristics of a typical moderately reverberant room. This is done by configuring the simulated room to have a dimension of 3.8 m×4.0 m×2.3 m and adjusting the wall absorption characteristics to produce an RT60 time of 0.25 s. Note that these parameters were intentionally chosen to match those reported in the "plexiglass (PLEX)" condition in an earlier study by Marrone et al. (2008).

Time-compressed reverb: The time-compressed reverb condition was identical to the reverb condition, except that the target speech signal was modified using the pitch-synchronous overlap and add (PSOLA) algorithm in the PRAAT software package (Boersma and Weenink, 1996) to increase its speaking rate by 50% (i.e., time-compressed to 66% of its normal length). The Target Stimulus should be time compressed using a PSOLA technique as described in Moulines, E., & Charpentier, F. (1990). Pitch-synchronous waveform processing techniques for text-to-speech synthesis using diphones. Speech communication, 9(5-6), 453-467, is hereby incorporated by reference. This stimulus was designed to explore the difficulties that older and hearing impaired listeners often experience when trying to listen to fast speech in noisy environments (Gordon-Salant and Fitzgibbons, 2004).

Speech-shaped noise (SSN): In the SSN condition, both the left and right channels contain the target mixed with continuous speech-spectrum shaped noise taken from random segments of Track 68 of the QuickSIN CD.

To generate these modified signals, each existing electronic recording of speech signal-in-noise must first processed as follows:
a) time-aligning the speech and noise waveforms for each individual speech stimulus (each sentence);
b) separating the speech and noise waveforms by matching the amplitude of one of the two waveforms and subtracting it from the combined waveform; and
c) using cross-correlation to time-align the audio signal from a separately available audiovisual recording of the speech stimuli; Once each signal-in-noise is preprocessed, AV, NoSpi, spatial, reverb, and time-compressed reverb modification can be carried out. Steps of generating of prototype simuli conditions using QuickSIN are described in Example 1.

B. Hardware

An auditory test system for evaluating speech perception of this invention, comprises audio transducers, a hearing test device, a computer that is connected to the hearing test device and configured to use the test battery to generate and present to a listener a plurality of simulated conditions, which allows the test administer to verify and score listener responses, and generate a speech perception accuracy score based on the responses from the listener. The transducers may include but are not limited to air conduction transducers or bone conduction transducers, such as loudspeakers or headphones. A typical hearing test device may be consist of an audiometer meeting the specifications in ANSI S3.6-1996 American National Standard Specification for Audiometers. The stimuli described herein may be stored on a computer readable medium, such as a CD or as electronic files on an audiometer or a computer connected to an audiometer. The stimuli are be presented either by playing them with a compact disc player, computer connected to an electronic sound card, or other auditory playback device through the auxiliary input or by preloading them as electronic files in the audiometer control software.

The test battery includes at least standard, NoSπ and Time compressed Reverb simuli conditions, and may further include Spatial, AV, NoSπ+AV, Reverb and SSN simulation conditions.

In one embodiment, the test was conducted with the listeners in quiet sound-treated listening booths while wearing Sennheiser HDA200 audiometric headphones connected to a GSI-61 audiometer (Grason-Stadler). The stimuli were generated with a control PC running MATLAB with a soundcard (RME Hammerfall) connected to the auxiliary input of the audiometer.

C. Operational Use

To evaluate a listener's speech perception in complex listening environment, the test administer must first construct a test battery comprises a plurality of auditory simulation environments. The selected auditory simulation environments must include a N0Sπ or N0Spi stimulus condition, wherein is said target speech of said standard stimulus condition is phase shifted 180o in one ear; and a time-compressed reverb stimulus condition, wherein said standard stimulus condition is modified to simulate a spatial condition with the target speech presented in front of the listener, a first masking noise presented 90o to the left of the listener, and a second masking noise presented 90o to the right of the listener, each at a distance of 5 ft. in a simulated moderate reverberated room with a RT time of 0.25 s producing a Reverb stimulus condition, with speaking rate of said target speech of Reverb stimulus condition increased by 50%. The test battery may further include one or more of the following audio visual simulations environments:
a) a standard stimulus condition, which is a diotic presentation of a target speech in the presence of a masking noise;
b) an audiovisual stimulus condition (AV), wherein a video signal corresponding to said standard stimulus condition and said standard stimulus condition are simultaneously presented to said listener;
c) an AV+N0Sπ stimulus condition, wherein a video signal of the corresponding to said standard stimulus condition and said N0Sπ stimulus condition is simultaneously presented to said listener;
d) an spatial stimulus condition, wherein said which said standard stimulus condition is modified to simulate a spatial condition with the target speech presented in front of the listener, a first masking noise presented 90o to the left of the listener, and a second masking noise presented 90o to the right of the listener, each at a distance of 5 ft.;
e) an Reverb stimulus condition, wherein said standard stimulus condition is modified as to be presented in a simulated moderate reverberated room with a RT time of 0.25 s;
f) a Speech-shaped noise (SSN) stimulus condition, which is a diotic presentation of said targeted speech and a continuous speech-spectrum shaped noise masker.

The listener is placed in quiet sound-treated listening booth and required to wear an audiometric headphone (such as Sennheiser HDA200 headphone) connected to an audio testing device (such as a Grason-Stadler GSI-61 audiometer). The stimuli were generated based on the selected test battery with a control PC with a soundcard (RME Hammerfall) connected to the auxiliary input of the audiometer running testing software such as MATLAB®. The listener is asked to perform speech recognition task such as those identified in QuickSIN manual in each of the auditory stimulus conditions. The result of the speech recognition task is then scored in accordance with the procedure outlined in the QuickSIN manual (Appendix B), which is hereby incorporated. For example, the test administer first estimates the $SRT_{50}$ value of a listener. The identify listener as having speech-in-noise deficit, if their $SRT_{50}$ greater than the cutoff SRT. The cutoff SRT may be determined by setting a range of normal performance. For example, SRT data of a normative sample of individuals with clinically normal hearing are collected. The 95th percentile score (cutoff SRT) within that population is identified such that 95% of normal-hearing listeners have an SRT score less than or equal to a cutoff SRT.

The present invention may also be used to evaluate the effectiveness of a hearing prosthesis or hearing protection device on speech perception. The test administer must first construct a test battery comprises a plurality of auditory simulation environments. The selected auditory simulation environments must include a N0Sπ or N0Spi stimulus condition, wherein is said target speech of said standard stimulus condition is phase shifted 180o in one ear; and a time-compressed reverb stimulus condition, wherein said standard stimulus condition is modified to simulate a spatial condition with the target speech presented in front of the listener, a first masking noise presented 90o to the left of the listener, and a second masking noise presented 90o to the right of the listener, each at a distance of 5 ft. in a simulated moderate reverberated room with a RT time of 0.25 s producing a Reverb stimulus condition, with speaking rate of said target speech of Reverb stimulus condition increased by 50%. The test battery may further include one or more of the following audio visual simulations environments:

a) a standard stimulus condition, which is a diotic presentation of a target speech in the presence of a masking noise;

b) an audiovisual stimulus condition (AV), wherein a video signal corresponding to said standard stimulus condition and said standard stimulus condition are simultaneously presented to said listener;

c) an AV+N0Sπ stimulus condition, wherein a video signal of the corresponding to said standard stimulus condition and said N0Sπ stimulus condition is simultaneously presented to said listener;

d) an spatial stimulus condition, wherein said which said standard stimulus condition is modified to simulate a spatial condition with the target speech presented in front of the listener, a first masking noise presented 90o to the left of the listener, and a second masking noise presented 90o to the right of the listener, each at a distance of 5 ft.;

e) an Reverb stimulus condition, wherein said standard stimulus condition is modified as to be presented in a simulated moderate reverberated room with a RT time of 0.25 s;

f) a Speech-shaped noise (SSN) stimulus condition, which is a diotic presentation of said targeted speech and a continuous speech-spectrum shaped noise masker.

The listener is placed in quiet sound-treated listening booth and required to wear an audiometric headphone (such as Sennheiser HDA200 headphone) connected to an audio testing device (such as a Grason-Stadler GSI-61 audiometer). The stimuli were generated based on the selected test battery with a control PC with a soundcard (RME Hammerfall) connected to the auxiliary input of the audiometer running testing software such as MATLAB®. The listener is asked to perform speech recognition task such as those identified in QuickSIN manual in each of the auditory stimulus conditions. The result of the speech recognition task is then scored in accordance with the procedure outlined in the QuickSIN manual (Appendix B), which is hereby incorporated. For example, the test administer first estimates the $SRT_{50}$ value of a listener. The hearing prosthesis or hearing protection device fails the speech perception test, if the listener's $SRT_{50}$ greater than the cutoff SRT. The cutoff SRT may be determined by setting a range of normal performance. For example, SRT data of a normative sample of individuals with clinically normal hearing are collected. The 95th percentile score (cutoff SRT) within that population is identified such that 95% of normal-hearing listeners have an SRT score less than or equal to a cutoff SRT.

Examples 1-3 shows validation trials of the prototype test battery developed according to this invention. These clinical trials are described in details in Phatak S A, Sheffield B M, Brungart D S, Grant K W. (May/June 2018), "Development of a Test Battery for Evaluating Speech Perception in Complex Listening Environments: Effects of Sensorineural Hearing Loss." *Ear Hear.* 39(3):449-456, and Brungart D S, Sheffield B M, Kubli L R. (August 2014). "Development of a test battery for evaluating speech perception in complex listening environments." *J Acoust Soc Am.* 136(2):777-90, which are hereby incorporated by reference in their entireties.

Example 1: Development of the Prototype Stimuli Using QuickSIN Sound Track

All of test stimuli conditions (i.e. simulation environment) used in Examples 1 and 2 were constructed by modifying the stimuli that were developed from the original QuickSIN test. The QuickSIN is a clinical speech-in-noise test designed to rapidly determine the minimum signal to noise ratio (SNR) a listener requires to correctly identify 50% of the keywords in a low-context sentence in the presence of a four-talker babble noise. The minimum SNR required for 50% correct keyword identification performance is referred to as the "speech reception threshold" or the SRT50. The QuickSIN estimates the SRT50 value of a listener by presenting a series of six sentences from the IEEE corpus at SNR values ranging from 25 to 0 dB. The target talker is always presented at a fixed level, usually at 70 dB hearing level (HL), and the SNR value is varied by adjusting the masker level relative to the target to present the first sentence at 25 dB SNR and then to decrease the SNR on each successive stimulus presentation by increasing the level of the noise by 5 dB. Each IEEE sentence contains five key words, and the listener's performance is scored by determining the number of correctly identified keywords at each SNR. The clinical test is scored with a simplified formula based on the work of Tillman (Wilson et al., 1973) that assumes (a) that the psychometric function is symmetric around the 50% correct point and (b) that all listeners would be able to obtain 100% correct responses at an SNR of +30 dB and that none would obtain more than 0% correct responses at an SNR value of −5 dB. Under these assumptions, the SRT50 value for the QuickSIN test can be obtained simply by subtracting the number of correct keywords on the test (of a maximum score of 30) from 27.5.

These stimuli, which are provided in the form of a series of audio tracks on a compact disk, all consist of a female target talker reading sentences from the IEEE corpus IEE (IEEE Subcommittee, 1969) in a babble noise background with four interfering talkers (three females and one male). In the standard clinical tracks on the CD (tracks 3-20), the target and noise have been mixed at a specified SNR diotically with the two channels being identical. However, the CD also includes an additional version of each of these tracks where the target talker is presented in quiet on one channel, and the four-talker babble is presented at a constant level on the other channel (split tracks). By analyzing these two versions of each track, it was possible to construct stimuli that preserved the relative levels and the temporal relationships between the target and masking waveforms in the original QuickSIN stimuli but allowed the target and masking signals to be processed independently and recombined with any desired shift in the SNR.

The QuickSIN test was selected as the basis for the expanded functional test for a variety of reasons. Some of these reasons are related to the intrinsic features of the test and its utility as a clinical measure of speech-in-noise performance:

(1) The test is very efficient, allowing an estimate of SRT50 to be made in six sentence presentations that only take about a minute to complete.

(2) The test has been demonstrated to have a high degree of test-retest reliability (Killion et al., 2004) with a typical difference of only 1.9 dB across consecutive administrations to the same listener (using different word lists).

(3) The test is well accepted by clinical audiologists and has been widely used in both clinical and research applications since its introduction in 2004.

Two other reasons for selecting the QuickSIN test are more technical in nature but still very important:

(1) The test has been validated for a total of 18 six-sentence word lists, including 12 equivalent individual lists and 3 additional pairs of lists that are equivalent to the individual lists when their results are averaged together. This makes the test suitable to modifications that require the test to be repeated many times under different acoustic conditions with the same listener.

(2) The source materials of the test were available, including clean recordings of both the target and masker waveforms in each stimulus as well as the original audiovisual recordings of the stimuli in the audio version of the validated clinical test.

These properties make the QuickSIN a suitable choice as basis of prototype battery of test of this invention. To construct prototype test stimulus conditions for this invention, the single condition speech-in noise test of QuickSIN is expanded into a more comprehensive battery of functional hearing tests that address a wide range of factors that might influence speech perception, including availability of audio-visual speech cues, and the ability to take advantage of binaural and spatial speech segregation cues. As described below and illustrated in FIGS. 1A and 1B, this is accomplished by adapting the monaural, audio-only stimuli in the clinical QuickSIN test into a set of eight different stimulus conditions, each addressing a different type of complex listening environment.

Figure 1A:
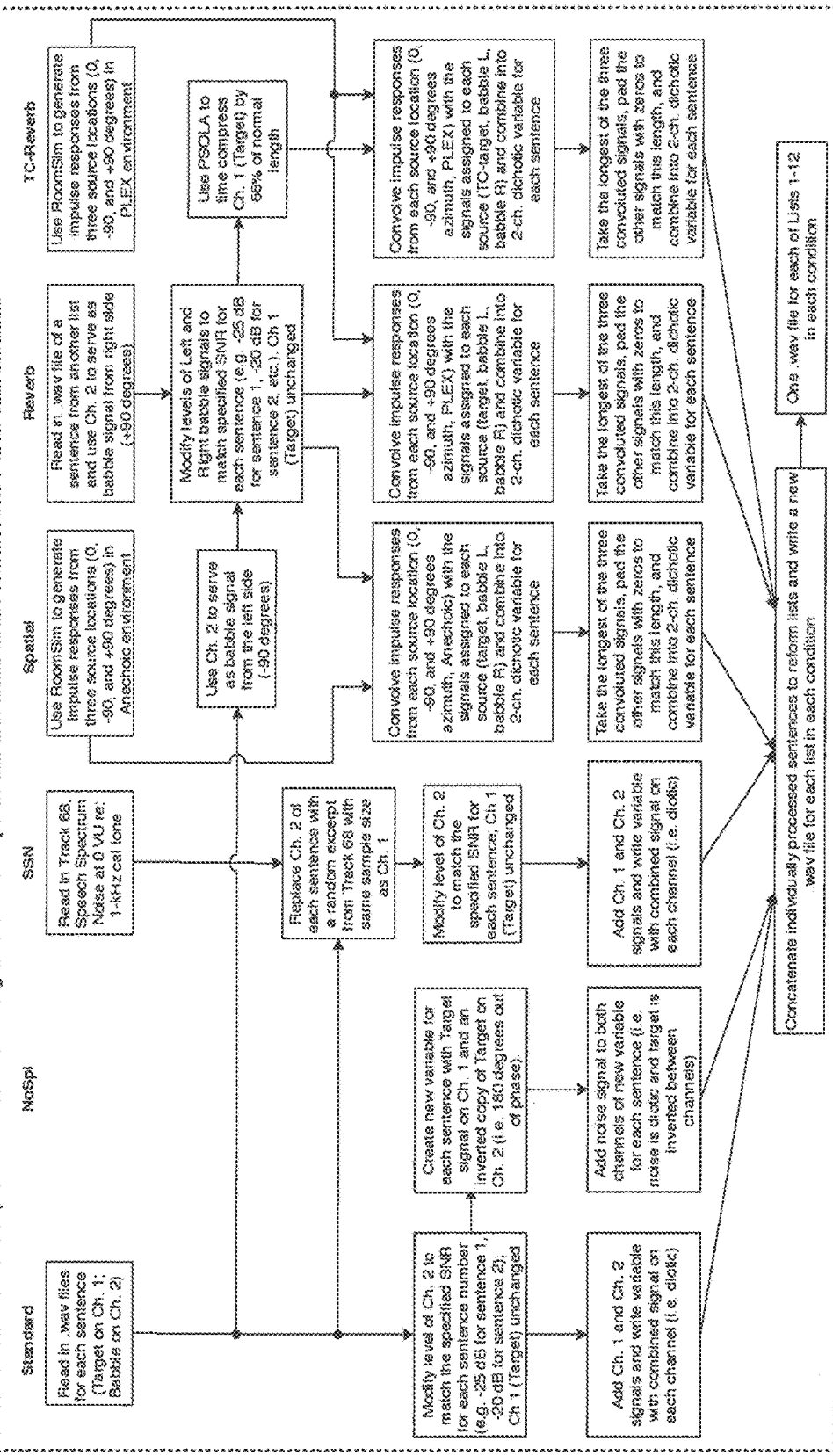
FIG. 1A shows a flow chart of procedures 1 and 2 of the development of prototype stimuli by modifying quickSIN.
Figure 1B:
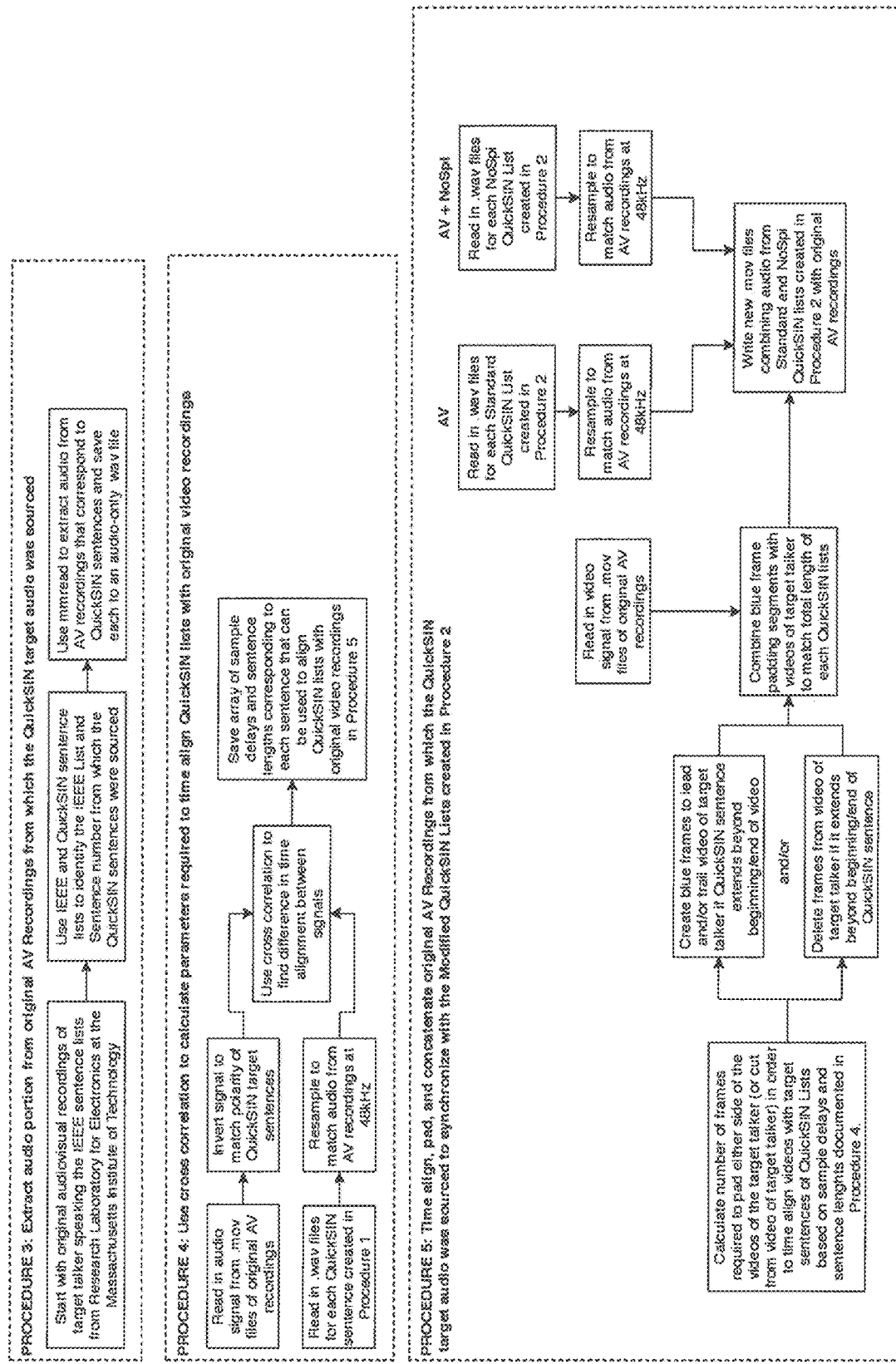
FIG. 1B shows a flow chart of procedure 3-5 of the development of prototype stimuli by modifying quickSIN.

FIGS. 1A and 1B shows the procedures took to generate each of the eight different stimulus conditions from Quick-SIN test. As shown in FIG. 1 Procedure 1, individual tracks (corresponding to QuickSIN lists 1-12) from the QuickSIN CD are separately saved. Each individual sentence from QuinckSIN lists 1-12 are then saved into separate files with the talker (target speech or target signal) presented on channel 1, and 4-talker babble noise (noise masker) presented on channel 2. In Procedure 2, MATLAB® is used to process each individual sentence according to the audio-only signals, and then recombined into sentence lists 1-12 for each condition. As shown in FIG. 1A, the standard four-talker babble condition is created by modifying the level of masker noise (channel 2) to match the specified SNR for each sentence number (i.e., the first sentence is set to 25 dB lower than the target speech and the sixth sentence is set to the same level as the target speech). The target speech and modified masker noise are then combined, and presented binaurally on both channels 1 and 2. NoSπ stimulus condition is constructed by presenting target inverting the target signal in channel 2 relative to channel 1 before combining with the noise signal on channels 1 and 2. SSN is processed by replacing the masker noise (channel 2) of each sentence with a random excerpt from track 68 (continuous speech spectrum shaped noise). The masker noise on channel 2 is modified to match the specified SNR for each sentence and combined with channel 1 target speech to generate a combined signal, which is then presented on both channels 1 and 2. For the spatial, reverb and TC+Reverb conditions, Channel 2 (masker noise) of the current list/sentence is selected to serve as the noise signal for the left side (babble L), and Channel 2 (masker noise) from a different list/sentence is selected to serve as the noise signal for the right side (babble R). Noise signals of both the left and right side are modified to match the specified SNR for each sentence. These noise signals are then processed differently to generate the spatial, Reverb and TC+Reverb conditions. To generate the spatial condition, the MATLAB® RoomSim function is used to convolve impulse responses from each source location (0, −90, and +90 degrees azimuth) with the signals assigned to each source (target, babble L and babble R). The room characteristics are set to replicate an anechoic environment. The target speech signals are separately combined with the babble L and babble R signals and presented as a 2 channel dichotic variable for each sentence. The two shorter convoluted signals are padded with zeros to match the length of the longest of the three convoluted signals, and combined into a 2 channel dichotic variable for each sentence. To generate the reverb condition, the MATLAB® RoomSim function is used to convolve impulse responses from each source location (0, −90, and +90 degrees azimuth) with the signals assigned to each source (target, babble L and babble R). The room characteristics are set to replicate an anechoic environment. The simulated room is set to have dimensions of 3.8 m×4.0 m×2.3 m and wall adsorption is adjusted to produce an Reverberation Decay Time to 60% (RT60) of 0.25 s. The target speech signals are separately combined with the babble L and babble R signals and presented as a 2 channel dichotic variable for each sentence. The two shorter convoluted signals are padded with zeros to match the length of the longest of the three convoluted signals, and combined into a 2 channel dichotic variable for each sentence. The TC+Reverb condition is generated by first using the pitch-synchronous overlap and add (PSOLA) algorithm on the target speech signal to increase its speaking rate by 50%. The MATLAB® RoomSim function is then used to convolve impulse responses from each source location (0, −90, and +90 degrees azimuth) with the signals assigned to each source (target, babble L and babble R). The room characteristics are set to replicate an anechoic environment. The simulated room is set to have dimensions of 3.8 m×4.0 m×2.3 m and the wall adsorption is adjusted to produce an RT60 ime of 0.25 s. The target speech signals are separately combined with the babble R and babble L signals and presented as a 2 channel dichotic variable for each sentence. The two shorter convoluted signals are padded with zeros to match the length of the longest of the three convoluted signals, and combined into a 2 channel dichotic variable for each sentence. After processing, individually processed sentences are recombined to create a new audio track for each of sentence lists 1-12 presented in each condition. FIG. 1B shows how AV and AV+NoSπ conditions are produced.

According FIG. 1B, audio signals are extracted from AV recordings that correspond to QuickSIN sentence lists 1-12 to generate audio only files to be used as time references for video alignment (procedure 3). Cross-correlation is made between audio of original video recordings and the target audio of the standard QuickSIN lists to determine parameters required to time align the video recordings with their corresponding sentences in the QuickSIN lists (procedure 4). In procedure 5, the individual AV recordings of each sentence are padded with blue screen frames, ordered, and synchronized with the modified QuickSIN lists/conditions generated in procedure 2.

Example 2: Evaluate Speech Perception in Normal Hearing Participants in Complex Listening Environment 1. Methods
  A. Participants
  A total of 49 volunteer listeners (28 male, 21 female) with normal hearing participated in the study. All were recruited from the local community of employees, military members, and military dependents at the Walter Reed National Military Medical Center in Bethesda, Md. Their ages ranged from 20 to 45 yr (mean: 28.3 yr, r¼ 6.5 yr). All were given a full audiometric evaluation as part of their participation in the study, and all had hearing thresholds less than or equal to 20 dB in both ears at 250, 500, 1000, 2000, 3000, 6000, and 8000 Hz.
  B. Equipment
  The experiment was conducted with the listeners in quiet sound-treated listening booths while wearing Sennheiser HDA200 audiometric headphones connected to a GSI-61 audiometer (Grason-Stadler). The stimuli were generated with a control PC running MATLAB® with a soundcard (RME Hammerfall) connected to the auxiliary input of the audiometer.
  C. Procedure
  Each listener participated in two sessions of the QuickSIN task that were conducted as part of a larger experiment looking at a number of different subtasks related to speech perception. In the first session, each listener conducted a set of SRT measurements in each of the eight listening conditions of the experiment in random order. In the second session, they conducted another series of SRT measurements in each of the eight listening conditions of the experiment but with the order of the conditions reversed. Thus across the two sessions, each listener conducted a total of 16 sets of SRT measurements with two measurements collected in each of the eight listening conditions in a pseudorandom and counterbalanced fashion.
  Each set of SRT measurements consisted of two parts: A method of adjustment task and a speech perception task. The total time required to complete these two tasks varied by subject, but across all the listeners, the median time to complete a full set of SRT measurements in a single listening condition was approximately 100 s.
  1. Method of Adjustment Task
  The first part of each set of SRT measurements consisted of a method of adjustment task where listeners were asked to listen to a continuous stream of IEEE sentences at a fixed level [70 dB sound pressure level (SPL)] and adjust the level of the noise masker to the points they identified as their SRT0 and SRT100 thresholds. At the start of the task, listeners were presented with a continuous stream of sentences at 70 dB SPL in quiet. Then they were asked to use the slider on a MIDI control box (Beyerdynamic BCF2000) to adjust the level of the noise just up to the point where they could still hear the words but could no longer understand anything being said. Once they reached this point, they pressed a button to record their response, which was recorded as the SRT0 point. Then they were asked to use the slider to turn down the noise to the point where they were just able to understand all of the words spoken by the target talker. Once they reached this point, they pressed another button, and this was recorded as the SRT100 point for that listener. To prevent listeners from using the visual location of the slider as a reference, a random offset was introduced into the mapping between the position of the slider and the level of the masker signal at the start of each repetition of the method of adjustment task.
  2. Speech Recognition Task
  The second part of each set of SRT measurements consisted of a speech recognition task that used the standard QuickSIN procedure to estimate an SRT50 value for each listener. As in the standard QuickSIN task, the listeners heard up to six sentences, each with five keywords, presented at SNR values that started at a high level and decreased by 5 dB after each sentence. After each trial, the listeners were asked to repeat back the sentence, and an experimenter scored the test by clicking on the correct and incorrect words in a MATLAB® graphical interface. The sentences used in this portion of the experiment were drawn directly from the sentence lists used in the original QuickSIN test. The lists were selected in random order in such a way to ensure that no list was ever repeated twice for the same listener. In cases where one of the four "paired" QuickSIN lists was used (i.e., lists 13-14 or 15-16), the software was designed to ensure that both lists in the pair were collected in the same listening condition for that subject. In other words, if a listener received list 15 in the spatial condition in the first session, they always received list 16 in the spatial condition in the second session.
  As in the standard QuickSIN, the SRT50 in each condition was estimated by using the Tillman-Olsen procedure to convert the number of correct responses to an estimate of the SRT. One slight difference between the sentence lists used in this task and the standard QuickSIN is that the SNRs used in the speech recognition task varied over a range that was defined by the method of adjustment task rather than over a fixed range of SNRs. The initial SNR was always set to a point 12.5 dB higher than the midpoint between the SRT0 and SRT100 values obtained from the method-of-adjustment portion of the task. Thus at the end of a list the SRT50 estimate was calculated by adding 2.5 (i.e., half the step size) to the initial (i.e., highest) SNR tested in that list and then subtracting the number of correct responses. Note that this calculation parallels the one used in the standard clinical QuickSIN, where the initial SNR is always set to 25 dB, the step size is 5 dB, and the SRT50 is always calculated by subtracting the number of correct responses from 25 dB+2.5 dB=27.5 (Killion et al., 2004). Also note that in cases where listeners identified zero keywords in two consecutive sentences, the list was terminated and the subjects were assumed to receive a zero score on all the remaining key words in that list.
  II. Results and Discussion
  A. Effects of Listening Condition on Objective SRT
  FIG. 2 shows the mean estimate of the 50% SRT for each condition of the experiment, as calculated using the Tillman-Olsen technique used in the original QuickSIN test (Killion et al., 2004; Wilson et al., 1973). The results have been divided into three panels. The left panel shows performance in the four-talker babble conditions, where the masker was derived directly from the four-talker babble track on the QuickSIN CD.

The leftmost point in the left panel shows performance in the baseline four-talker babble condition of the experiment, which was essentially identical to the current clinical version of the QuickSIN test. This point shows that the mean SRT value in the babble condition was 1.0 dB, which is very close to the 1.9 dB mean SRT value reported in the original normative evaluation of the QuickSIN. Moving from that point to the right, we see that the addition of visual cues in the AV condition reduced the SRT by approximately 4 dB, which is comparable to the AV advantage reported for IEEE sentences by Grant et al. (1998). Similarly, the addition of BMLD cues in the N0Spi condition resulted in a reduction in the SRT of approximately 5.7 dB, which is comparable to the roughly 6 dB BMLD for speech reported by Levitt and Rabiner (1967). The combination of AV and BMLD cues in the AV+N0Spi cues resulted in a net reduction in the SRT of 9.1 dB, which is very close to the 9.8 dB reduction that would be predicted from the sum of the visual benefit in the AV condition and the BMLD in the N0Spi condition. We are unaware of any studies that have specifically examined the performance benefits obtained from stimuli that contain both audiovisual and BMLD cues, but the fact that the two benefits are very nearly additive suggests that they must be obtained from enhancing different cues in the perceived speech signals. This is consistent with the idea that the visual cues effectively enhance the "place and manner" cues in a voice waveform (which tend to occur at high frequencies), whereas the BMLD effectively enhances the voicing cues in a speech signal [which tend to occur at lower frequencies (Levitt and Rabiner, 1967)].

The middle panel of FIG. 2 shows performance in the three spatial conditions of the experiment, where the masker was composed of two spatially separated four-talker babble tracks. In the baseline spatial condition, the mean SRT50 was 0.7 dB, which was very close to the $SRT_{50}$ found in the baseline babble condition. However, it should be noted that the similarity in these two SRT50 values is somewhat misleading because the spatial condition simulates a situation where the single four-talker babble noise in the baseline condition is replaced by two independent spatially separated four-talker babble noises that are each presented at the same overall level as the original noise track. Thus the spatial SRT50 really represents a case where the spatial release obtained by processing the target and masker waveforms with HRTFs almost exactly counterbalances the 3 dB decrease in overall SNR and the reduction in "dip-listening" opportunities caused by the addition of a second independent four-talker babble to the stimulus. Because of these differences, we believe it is only appropriate to make direct comparisons across conditions with the same number of masking talkers, so we have divided the results from the four-talker conditions and the eight-talker conditions into separate panels when displaying the results.

The SRT for the spatial condition increased 4.3 dB when a modest amount of room reverberation was added to the signal and by an additional 4.7 dB when the target talker in the reverberant environment was modified to speak at a rate 50% faster than the normal speaking rate in the IEEE corpus. Thus it seems that even normal hearing listeners have a substantial amount of difficulty understanding speech in listening environments that combine modest levels of room reverberation with speech signals that are produced without the slow and clear articulation normally used in clinical speech tests. These are exactly the types of speech distortions that are likely to occur in the public spaces that the elderly and hearing-impaired listeners tend to report having the most difficultly with, like bars, restaurants, and cafeterias.

The right panel of FIG. 2 shows performance in the SSN condition of the experiment, which produced a mean SRT50 value of 0.4 dB. The SSN condition differs from the standard babble condition in two ways. First, it contains a noise masker that is acoustically much different than the target speech signal and therefore much less likely to cause informational masking than the standard four-talker babble (Brungart, 2001). However, this reduction in informational masking is apparently offset by the elimination of pauses and gaps in the four-talker babble that would ordinarily let listeners "dip listen" to portions of the target signal that occur at a relatively high local SNR. The net effect is that listeners performed very similarly with the SSN and four-talker babble maskers.

B. Effects of Listening Condition on Method of Adjustment Estimates

FIG. 3 compares the mean values obtained in the two subjective SRT values obtained in each listening condition to the objective SRT50 values that were calculated using the method described in the previous section. In general, these results show very good agreement between the pattern of performance obtained across the different listening conditions for the subjective SRT100 and SRT0 values and the general pattern obtained using the traditional SRT50 measure of speech perception. As would be expected, the mean SRT50 value in each of the eight conditions fell somewhere between subjective estimates obtained for the SRT0 and the SRT100. In most cases, the mean SRT50 value fell roughly halfway between the SRT0 and the SRT100 estimates. However, there were two clear exceptions. The first was in the AV conditions of the experiment, where the SRT0 value was only slightly below the SRT50 value. In these conditions, it is likely that the visual cues available in the stimulus rapidly became more useful when a small amount of auditory information was introduced. This is consistent with the audio-only and audiovisual performance curves for IEEE sentences in noise presented by Grant and Braida (1991), which showed much more rapid increase in performance with SNR at low SNR values in the AV condition than in the audio alone condition.

The other condition where the SRT50 value did not fall in the middle of the SRT0 and the SRT100 estimates was the TC+reverb condition. In that condition, the SRT100 condition was very similar to the SRT50 condition. The reasons for this are not clear at this time, but they may be related to the fact that the SNR value was already very high in this condition (>10 dB), which may have given the listeners the impression that they would not benefit from additional increases in SNR.

C. Slopes of Psychometric Functions

When analyzing the performance of individual listeners in speech perception tasks, it is sometimes useful to obtain information not only about the absolute decibel level of the speech perception threshold but also about the slope of the performance curve in the vicinity of the threshold. This additional information makes it possible to make a rough prediction of how much performance in the task will be improved by slight increases in the SNR around the SRT50 value (or, conversely, how quickly performance will drop when the SNR falls below the SRT). Although the modified Tillman-Olsen technique used to estimate the SRT50 values in the QuickSIN test was not originally intended to provide information about slope, it does require the collection of response data at a minimum of six different SNR values in each individual test condition. These six data points made it possible to estimate the slope of the psychometric function for each listener in each condition of the experiment using the following procedure. First, the response data from each individual list were linearly interpolated to create an estimate of the percentages of correct responses at SNR values that ranged from −12.5 to +12.5 dB (in 5 dB steps) around the SRT50 value estimated in that condition. This produced an estimate of the psychometric function $P_C(SNR)$ for that individual list and that individual listener, where $P_C$ is the percentage of correct responses and SNR is the SNR of the stimulus presentation. The psychometric function was then forced to be symmetric around the SRT50 estimate (as is assumed by the Tillman-Olsen method) by setting $$P'_C(SNR-SRT_{50})=(P'_C(SNR-SRT_{50})+(1-P_C(SRT_{50}-SNR)))/2$$

The psychometric functions were then averaged together for the two lists collected in the same condition for the same listener, and the resulting averaged psychometric function was then fit using a logistic function that was constrained to start at a value of 0% correct responses at an SRT 17.5 dB below the SRT50 value and end at a value of 100% correct responses at an SRT value 17.5 dB above the SRT50 value. FIG. 3 shows an example of the calculation of the maximum slope value for a typical normal hearing listener in the standard four-talker babble condition of the experiment. Note that in cases where the logistic fit generated a slope greater than 45% per decibel, the slope was set to equal 45% dB, which is approximately equal to the shallowest slope of a psychometric function that could reasonably transition from 0% correct responses to 100% correct responses within a single 5 dB step in SNR in the test.

FIG. 5 shows the mean slope values obtained for the normal-hearing listeners in each condition of the experiment. A one-factor within-subjects analysis of variance (ANOVA) on this data indicates that the main effect of sentence condition identification was significant ($F_{(1,7)}=127$, $p=0.04$).

A post hoc analysis indicated that there were significant differences between the two conditions with the highest slopes (babble and SSN) and the three conditions with the lowest slopes (AV, AV+$N_0S_{pi}$, and TC+reverb) but not between the other conditions.

The relatively high mean slope value (roughly 15 percentage points per decibel) in the speech-shaped noise condition probably occurred because the masker was a continuous noise with no spectro-temporal "gaps" that might allow the listener to obtain information from spectro-temporal regions of the stimulus where the local SNR was relatively high due to a temporary "dip" in the level of the babble masker. When present, these spectro-temporal gaps generally result in a flattening of the psychometric function.

The second highest mean slope (14.3 percentage points per decibel) occurred in the baseline Babble condition of the experiment. This relatively high slope was probably the direct result of the care that the developers of the original QuickSIN test devoted to selecting target and masker stimulus pairs that would be perfectly balanced in terms of overall intelligibility for each phrase contained in each standardized QuickSIN list. In effect, the objective of this selection process was to choose stimuli that would produce the steepest psychometric functions possible within each sentence list. This equalization was not done for the target and masking stimuli used in the other conditions of the experiment; this probably resulted in more variation in intelligibility across the sentences in each list and, as a direct consequence, a less steep overall slope in the psychometric function. The psychometric functions with the lowest slopes (roughly 11.5-12 percentage points per decibel) occurred in the two AV conditions and in the TC+reverb condition of the experiment. The relatively low slopes in the AV conditions are not surprising because listeners in these conditions had access to a visual information component that contributed a fixed amount of information that was not dependent on the SNR value of the stimulus. Most experiments that have measured psychometric functions in A only and AV conditions with the same stimuli have reported lower slopes in the AV conditions, presumably because of the SNR-independent contribution made by the visual cues in these conditions. The reasons for the relatively low slope in the TC+reverb condition are not known, but the low slope value suggests that there was slightly more variability across the intelligibility of the individual phrases in that condition than there was in the other conditions of the experiment.

All of the other conditions produced psychometric functions with slopes of approximately 13 percentage points per decibel. While these slopes were not quite as high as those achieved for the carefully calibrated four-talker babble condition, they are comparable to other published norms for the slopes of psychometric functions for sentences in stationary noise maskers. For example, Kryter (1962) provides data showing that speech intelligibility for unknown sentences has a maximum slope of approximately 13% for each 1 dB increase in SNR in stationary SSN.

D. Test-Retest Reliability

Each listener in the experiment participated in two independent repetitions of each SRT value in each of the eight listening conditions. This makes it possible to derive an estimate of the test-retest reliability of each SRT measure by averaging together the absolute difference between the two SRT estimates obtained from the same subject in each condition. These absolute differences are plotted in FIG. 6.

In the baseline four-talker babble condition, the two estimates of SRT50 differed by an average of 2.3 dB. If the distribution of responses in a particular condition is assumed to be a Gaussian variable, this corresponds to an across-subject, across-list standard deviation in the SRT score of 1.4 dB, which is slightly lower than the 1.9 dB value reported for across-subject, across-list standard deviation in the original normative evaluation of the QuickSIN (Killion et al., 2004).

For the SRT50 measurements (open circles in the figure), test-retest reliability was similar across all the different listening conditions except in the two AV conditions, which had test-retest differences that were roughly 50% larger than those in the other conditions. Not surprisingly, this suggests that the sentences that were selected to produce roughly comparable difficulty across the 16 lists in the audio-only QuickSIN test may not be perfectly equalized across lists in the AV condition.

Test-retest reliability with the subjective estimates of the SRT0 values varied somewhat across the conditions but, in general, it was comparable to the test-retest reliability obtained with the objectively measured estimates of SRT50.

In the baseline babble condition, the test-retest reliability was very similar for the SRT50 and SRT0 estimates. This demonstrates that listeners are very reliably able to make repeated estimates of the point where they are no longer able to understand any of the words in a sentence.

Test-retest reliability was not as good with the subjective SRT100 estimates as it was for the other two types of SRT measurements. In most cases, the two SRT100 estimates differed by 3.5-4 dB, compared to approximately 2.5 dB in the most reliable conditions with the SRT50. It is notable, however, that the best test-retest reliability for the SRT100 estimates occurred in the babble and SSN listening conditions, which also had the steepest psychometric functions.

E. Correlation Across Listening Conditions

Although the eight conditions tested in the experiment all represent substantially different listening environments, there is reason to believe there may be some underlying similarities across the conditions that might cause listeners who perform relatively poorly in one condition to perform relatively poorly in other conditions as well. These underlying similarities can be captured by analyzing the correlations across the individual listener scores in the eight conditions of the experiment. These correlation values are shown in Table II, which shows the Pearson product-moment correlation coefficients for each pair of listening conditions in the experiment. Correlation values that were significant at the p<0.05 level (after Bonferroni correction for the 28 possible comparisons in the table) are highlighted in bold and marked with a single asterisk. Those that were significant at the p<0.005 level are marked with two asterisks.

TABLE I

Pearson correlation coefficient between two estimates of the three SRT values across all listeners. All correlations were statistically significant ($p < 1 \times 10^{-6}$).

| | Babble | $N_0S_\pi$ | AV | AV + $N_0S_\pi$ | Spatial | Reverb | TC + reverb | SSN |
|---|---|---|---|---|---|---|---|---|
| Babble | 1.0 | 0.25 | 0.34 | 0.38 | 0.15 | 0.34 | 0.14 | 0.36 |
| $N_0S_\pi$ | — | 1.0 | 0.49* | 0.66 | 0.50* | 0.38 | 0.46*** | 0.43 |
| AV | — | — | 1.0 | 0.53** | 0.39 | 0.36 | 0.26 | 0.43 |
| AV + $N_0S_\pi$ | — | — | — | 1.0 | 0.43 | 0.39 | 0.32 | 0.49* |
| Spatial | — | — | — | — | 1.0 | 0.43 | 0.43 | 0.36 |
| Reverb | — | — | — | — | — | 1.0 | 0.26 | 0.39 |
| TC + reverb | — | — | — | — | — | — | 1.0 | 0.32 |
| SSN | — | — | — | — | — | — | — | 1.0 |

In general, the correlations across the conditions are relatively weak, which is not surprising given that the entire test population consisted of relatively young listeners with clinically normal hearing who would not be expected to vary much in performance in standardized speech-in-noise test conditions. In particular, it is notable that relative performance in the standard "babble" condition was not significantly correlated with any other condition. In part, the relatively low correlation between the "babble" condition and the other conditions is a result of the relatively small variations that occur across normal-hearing listeners on the standard QuickSIN test. Indeed one of the main objectives in the design of the original QuickSIN stimuli was to minimize these types of variations. Nevertheless, the relatively weak correlation between the standard "babble" condition and the other seven conditions tested here is encouraging in two ways. First, it confirms that the additional listening conditions are sensitive to different aspects of speech perception that may impact performance in real-world environments but are not captured by the standard QuickSIN test. Second, it shows that the results of the experiment were not driven by non-auditory factors like working memory, vocabulary size, or overall motivation that would be expected to have a roughly equal impact on all the listening conditions tested.

Although most of the correlations were weak, there were some significant correlations across listening conditions in the experiment. As would be expected, the statistically strongest correlations were between the AV and AV+$N_0S_{pi}$ listening conditions (presumably representing a component of performance related to individual differences in speechreading efficiency) and between the $N_0S_{pi}$ and the AV+$N_0S_{pi}$ conditions (presumably representing a component of performance related individual differences in binaural processing). This binaural processing component also appeared to apply to the spatial and TC+reverb conditions, which were also both significantly correlated with the $N_0S_{pi}$ condition. Significant correlations were also found between the AV and $N_0S_{pi}$ conditions and between the AV+N0Sp and SSN conditions, although the underlying reasons for these correlations are not obvious.

F. Normative Performance for Each Listening Condition

In clinical applications, the purpose of the QuickSIN test is to assess whether the speech-in-noise scores of a particular listener fall within the range of what would be considered normal for a listener without any hearing loss. The cutoff value typically used for these assessments is the 5th percentile normal score (i.e., the score that 95% of normal-hearing listeners would be expected to meet or exceed on the test). Table II shows the mean, standard deviation, and $5^{th}$ percentile scores for each of the listening conditions tested in the experiment. These scores assume that each listener is tested twice in each condition and that the SRT values from these two data points are averaged together to obtain a single SRT value. Listeners with mean SRT scores that exceed the 5th percentile values would be considered to have a clinically significant SNR loss. It is worth noting that the critical 5th percentile SRT50 value for the baseline babble condition of the test (4.5 dB) is very similar to the 3.9 dB SRT value that is reported as a cutoff point where the mean SRT score averaged across two QuickSIN lists for an individual listener will fall outside the 95% confidence interval of expected scores for a listener with normal hearing (Killion et al., 2004). Thus it appears that the small methodological differences between the way the QuickSIN lists were tested in the original clinical validation and the way they were tested in this experiment did not result in any meaningful differences in the overall performance of normal hearing listeners in the baseline condition of the experiment.

G. Estimates of Population Distribution

The 5th percentile SRT cutoff values in Table II are useful for implementing the modified QuickSIN as a clinical test because they provide information about the interpretation of the scores of an individual listener who participates in a small number of SRT measurements using QuickSIN lists that are randomly selected from the 16 available lists. This enables the clinician to determine whether a participant falls outside the norm for each listening condition. However, in addition to accounting for the underlying variance in performance that occurs across individual listeners in each condition, these cutoff values also have to account for the purely random variations in performance that occur due to the limited amount of data collected in each condition with each subject. Thus it is not possible to use these results to make direct inferences about how underlying performance in each condition of the experiment would differ across the population of normal hearing listeners if it were possible to collect enough data to be certain about the performance level of each individual subject. However, it is possible to make inferences about the distribution of SRT values for each condition in the underlying population of normal hearing listeners by taking the overall intersubject variability measured in the experiment and attempting to factor out the component related purely to measurement error in the SRT value of each individual subject.

To obtain an estimate of intersubject variability in the underlying population, we need two variables. One is rind, an estimate of the variance of an individual listener on repeated measures of the same listening condition. In this experiment, we can obtain an estimate of the standard deviation rind of the SRT score that would be expected for an individual listener conducting multiple SRT measurements in the same condition directly from the mean absolute differences that were measured between repeated tests of a listening condition with different lists $\mu_{|A-B|}$. If we model the individual scores as Gaussian variables, and we assume that the individual score is obtained by averaging together the SRT scores from two lists that, on average, would be expected to produce SRT scores in the same listener that are $\mu_{|A-B|}$ apart, then it can be shown that $$\sigma_{ind} H 0.62 * \mu_{|A-B|}.$$

The second variable we need to estimate the underlying distribution of the population is $\sigma_{pop}$, the standard deviation across the mean SRT values actually obtained for different listeners in a given listening condition. Our goal is to estimate the standard deviation of the underlying population $\sigma_{und}$, which can be thought of as the perfect estimate of the variance across individual listeners that would be obtained if an infinite number of trials were conducted on each individual listener (thus bringing $\sigma_{ind}$ down to zero). This variable is related to the other two variables by the following relation $$\sigma^2_{pop} = \sigma^2_{ind} + \sigma^2_{und},$$

Which means that $$\sigma_{ind}(\sigma^2_{pop} - \sigma^2_{indiv.})$$

This manipulation is helpful because it allows us to separate the sampling error that occurs from a failure to accurately identify the true SRT value of an individual subject from the variation that is actually occurring in the underlying population of listeners. FIG. 7 shows a series of boxplots for the estimated distributions of performance across normal hearing listeners in each of the tests. The distributions for the SRT50 scores show that the majority of normal-hearing listeners would be expected to have SRT values within 61.5-2 dB of the median values shown in FIG. 7. This suggests that there are very meaningful differences across the different conditions we tested in this experiment and that these differences are large relative to the range of variation that would be expected in the normal population.

Even though the test-retest reliability scores of the SRT100 and SRT0 measures were comparable to those of the SRT50, FIG. 7 shows these subjective scores would be expected to be much more widely distributed across the population of listeners than the objective measure of the SRT. This probably reflects the fact that these subjective scores represent intrasubject variation in the criteria used to determine when a speech signal is 100% intelligible or 0% intelligible. Based on these results, it appears that it would not be appropriate to use these subjective scores to assess how an individual listener's performance in listening tasks compares to the overall population. However, these measures may be useful to compare to a listener's objective SRT score as the difference between the SRT100 score and the SRT50 score may be a good estimate of how much difficulty a listener is perceiving in a given listening environment.

TABLE II

Mean, standard deviation, and 5th percentile cutoff scores for the SRT0, SRT50, and SRT100 values obtained in each listening conditions of the experiment. These standard deviation and cutoff values assume each listener participates in two randomly selected QuickSIN lists (or two method of adjustment estimates) in each listening condition and that the SRT values recorded from these two data points are averaged together.

|  |  | Babble | $N_0S_\pi$ | AV | AV + $N_0S_\pi$ | Spatial | Reverb | TC + reverb | SSN |
|---|---|---|---|---|---|---|---|---|---|
| $SRT_{100}$ (dB) | Mean | 4.8 | 2.6 | −0.6 | −2.8 | 5.0 | 8.6 | 10.9 | 3.3 |
|  | SD | 5.9 | 6.3 | 6.7 | 6.9 | 6.4 | 6.0 | 5.6 | 5.7 |
|  | 5th Percentile | 13.0 | 12.3 | 8.8 | 5.3 | 14.6 | 17.7 | 22.2 | 12.3 |
| $SRT_{50}$ (dB) | Mean | 1.0 | −3.0 | −4.7 | −8.2 | 0.5 | 5.0 | 9.5 | 0.4 |
|  | SD | 1.8 | 2.9 | 2.5 | 3.4 | 2.4 | 2.1 | 2.6 | 1.8 |
|  | 5th Percentile | 4.5 | 1.6 | −0.2 | −3.5 | 5.9 | 8.8 | 14.3 | 4.2 |
| $SRT_0$ (dB) | Mean | −2.1 | −4.9 | −7.6 | −9.4 | −2.1 | 1.4 | 3.4 | −3.8 |
|  | SD | 3.3 | 3.3 | 3.4 | 4.1 | 3.7 | 2.8 | 3.2 | 3.7 |
|  | 5th Percenttile | 2.9 | 0.9 | −1.8 | −3.2 | 5.2 | 7.6 | 8.8 | 3.0 |

III. Conclusions

The purpose of this experiment was to develop and validate an efficient speech-in-noise test based on the QuickSIN that could be used to test speech perception ability in a wide variety of quasi-realistic listening environments both clinically and in research applications. In general, the results of the experiment are encouraging. The results show the following: (1) The standard four-talker babble QuickSIN stimuli used in the experiment produced mean SRT50 and test-retest reliability scores that were comparable to those obtained in other studies that have evaluated performance for QuickSIN stimuli in a population of normal-hearing listeners. (2) The modified stimuli used in the other seven listening conditions produced mean SRT50 scores that varied in a systematic way, and that the differences in performance across these conditions were consistent with those reported in previous studies that have examined the effects of similar stimulus manipulations on speech perception in normal-hearing listeners. For example, the effects of BMLD in the $N_0S\pi$ listening condition were similar to those reported by Levitt and Rabiner (1967), and the benefits of providing visual cues comparable to those reported by Grant and Walden (1996). (3) The test-retest reliability of the SRT50 values measured with the modified QuickSIN listening conditions was comparable to that obtained with the baseline four-talker babble QuickSIN condition. (4) The correlation in the SRT50 scores obtained in the different listening conditions was relatively low (with the exception of the expected correlations between the two $N_0S_{pi}$ conditions and the two AV conditions), suggesting that the different test conditions may address different underlying aspects of speech perception ability in normal-hearing listeners. (5) The differences in mean performance across the eight listening conditions were relatively large in comparison to the estimated standard deviation in performance across the underlying population of normal-hearing listeners, suggesting that there are meaningful differences across the listening conditions tested in this experiment and that it is possible to measure these differences with the modified QuickSIN stimuli presented here.

These results suggest that it should be possible to adapt the modified QuickSIN stimuli tested here into a standardized test, similar to the standard QuickSIN, for clinical or research applications that require speech perception performance to be measured across a variety of different listening configurations. The only minor modifications required would be (1) to set the SNR values tested to a fixed range rather than the adaptive range (based on the method of adjustment measures) used here and (2) to make some minor adjustments to account for any differences in difficulty across the 16 lists used in the experiment. It may be possible to make this adjustment simply by restricting the use of certain combinations of list number and listening condition that resulted in performance outside the normal range in a particular condition.

A second objective of this study was to evaluate the feasibility of using a subjective "method-of-adjustment" technique to evaluate SRTs as a possible alternative to the traditional QuickSIN test. In general, the results for normal hearing listeners reported here do not provide strong support for a method of adjustment task as a substitute for a traditional objective SRT measurement. Although the test-retest reliability of these measures was reasonably good, the results in FIG. 7 show that the intersubject variability was generally substantially higher in these subjective measures than it was in the objective SRT50 measure. This suggests that the subjective measures were not tracking the same differences in performance across the individual listeners as the SRT50.

However, the fact that the method-of-adjustment technique did not appear to be an adequate substitute for objective measures of SRT does not necessarily mean that it cannot be a valuable tool for assessing speech perception in normal and impaired listeners. Although intersubject variability was high with the subjective SRT0 and SRT100 measures, the within-subject variability of the SRT0 measure was generally as good, and in some cases better than, the within-subject variability of the objective SRT50. This would appear to mean that the method-of-adjustment technique is providing a reliable measure of some aspect of speech perception that is different than what is being captured with the objective SRT. It is most likely the case that the subjective scores are primarily related to differences in the criteria individual listeners apply when they are trying to estimate the SNR that produces "100% intelligibility" or "0% intelligibility." This could simply reflect individual preference, but it might also be related to the perceived difficulty or listening effort associated with each listening task (Sarampalis et al., 2009). If this is true, then these method-of-adjustment techniques could prove extremely valuable for evaluating the effects of different hearing aid configurations that might produce a reduction in perceived listening effort but have little or no measurable impact on performance in objective listening tasks. Now that the modified QuickSIN stimuli have been thoroughly evaluated with normal hearing listeners, the next step will be to use the same stimuli to evaluate listeners with various types of hearing impairment. Further research is now underway to complete this validation of the modified stimuli.

Example 3: Evaluating Speech Perception Normal and Hearing Impaired Participants in Complex Listening Environment I. Methods
A. Participants Participants between 19 to 57 years of age, who were either civilian staff members or were eligible for health care, were recruited for this study at Walter Reed Army Medical Center (Washington D.C.) or at Walter Reed National Military Medical Center (Bethesda, Md.). Audiometric thresholds were either taken from the listener's health records, if measured within six months of the start of testing, or were measured clinically as part of the study. Listeners were divided in three groups, H1 (normal to near-normal), H2 (mild), and H3 (moderate to severe), according to the hearing profiles described in the US Army standard for medical fitness [AR40-501] (U.S. Department of Army, 1960). Those in the H1 group were subdivided into two groups: normal-hearing (H1NH), having thresholds ≤20 dBHL between 250 to 8000 Hz, and mild hearing loss (H1HL). FIG. 8 shows the mean and standard errors in audiometric thresholds across listeners in each hearing profile group, and also lists gender and age statistics for each group. Data of the H1NH group was analyzed and presented in Brungart et al. (2014).

B. Stimuli

Prototype stimuli are generated by modifying quickSIN stimuli using procedures described in example 1 and shown in FIG. 1A and FIG. 1B. Participants were required to recognize IEEE (Institute of Electrical and Electronic Engineers, 1969) sentences spoken by a female talker, and presented in eight different conditions:

Babble: standard QuickSIN condition with four-talker babble masker

AV: Babble condition with audio-visual IEEE sentences

N0Sπ: Babble condition but phase of the target sentences shifted by 180° in one ear A V+N0Sπ: N0Sπ condition with audio-visual target sentences Spatial: using Head Related Transfer Functions, target set in front, and two four-talker babble maskers, one set to the left (−90°) and the other to the right (90°)

Reverb: Spatial conditions with reverberation (RT60=0.25 s) added to stimuli

Time compression and reverberation (TC+Rev): Reverb condition with target speech rate increased by 50% using pitch-preserving time compression (i.e., time compressed to 66% of the original length) prior to applying reverberation Speech-Spectrum Noise (SSN): standard QuickSIN condition with the babble replaced by continuous speech-spectrum C. Test Procedure The testing method and the test conditions were identical to those described in example 2 of this application. In each listening condition, participants first estimated the range of their psychometric curve using a method of adjustment. In this part, the participants were presented a continuous stream of IEEE sentences at 70 dB SPL, while they adjusted the background masker level using a slider. The participants first increased the masker to a level where they could hear the speech but no longer understand any word (i.e., SRT corresponding to 0% speech intelligibility (SRT$_0$)) and then decreased it to a level where they began to understand all the words (i.e., SRT corresponding to 100% speech intelligibility ($SRT_{100}$)).

The subjective SRT estimation was followed by a speech recognition task according to the standard QuickSIN procedure to measure the actual speech-in-noise threshold, denoted SRT50 (SRT corresponding to 50% speech intelligibility), for that condition. In this task, participants were required to hear and repeat back sentences from a QuickSIN list, each with five keywords, presented in the presence of background noise. The signal-to-noise ratio (SNR) of the first SNR was set to be 12.5 dB above the subjective SRT50 estimated for that condition, and the SNR of each subsequent sentence was decreased in 5 dB steps. The speech signal was set at 70 dB SPL, and the masker level was adjusted according to the SNR. Subject performance was scored based on the number of key words recognized correctly in each sentence. If a listener did not recognize any keyword correctly from a sentence, further sentences were not presented, assuming a score of zero for those sentences.

On the basis of the SRT calculation methodology in the standard QuickSIN procedure (Appendix A), the SRT50 was calculated by adding 2.5 dB to the SNR of first sentence and then subtracting the total number of keywords recognized correctly.

This procedure was repeated once for each condition, thus obtaining two estimates of each SRT. For the first set of SRT estimates, the eight listening conditions were presented in random order. In the second session, and for the second set, the order of the conditions from the first set was reversed, to counterbalance the presentation order effect. List numbers 1–16 from the QuickSIN CD were used in a pseudorandom order for estimating the SRT50 twice in each of the eight conditions. For each subject, list numbers 1-12 were randomly assigned across conditions, while list numbers 13-14 and 15-16 were always paired and were assigned to one of the six audio-only conditions because the video for these two list pairs was not available. The c e continuous stream of IEEE sentences for the subjective estimates (SRT0 and SRT100) was not from the QuickSIN CD, but rather from audiovisual recording of IEEE sentences by a different female talker, made using the same equipment and at the same time as the QuickSIN recordings. The total testing time per subject was about 25 to 30 min. This translates to about 3 to 4 min per condition, with about 2 mins required to obtain the subjective estimate (SRT0 and SRT100) and another 2 min to obtain the objective estimate (SRT50).

D. SSQ Questionnaire

An abbreviated version of the Speech, Spatial and Qualities of Hearing Scale (SSQ) questionnaire (Gatehouse & Noble 2004) was administered to listeners to sample their perceived difficulties in everyday speech communication. This abbreviated version consisted of 12 questions that were selected from the three subareas of the SSQ to be highly correlated with functional hearing handicap, weakly correlated with each other, or having operational relevance for individuals in challenging. The questions used in the abbreviated SSQ questionnaire are listed in Table III.

TABLE III

QUESTIONS IN ABBREVIATED QUESTIONNAIRE ALONG WITH THEIR ORIGINAL SSQ NUMBER.

| SSQ # | Original SSQ # | Question |
|---|---|---|
| 1 | Speech 14 | You are talking to someone on the telephone and someone next to you starts talking. Can you follow what's being said by both talkers? |
| 2 | Speech 12 | You are in a group and the conversation switches from one person to another. Can you easily follow the conversation without missing the start of what each new speaker is saying? |
| 3 | Speech 5 | You are talking to a person. There is continuous background noise, such as a fan or running water. Can you follow the conversation? |
| 4 | Spatial 8 | In the street, can you tell how far away someone is, from the sound of their voice or footsteps? |
| 5 | Spatial 13 | Can you tell from the sound whether a bus or truck (vehicle) is coming towards you or going away? |
| 6 | Spatial 17 | Do you have the impression of sounds being where you would expect them? |
| 7 | Spatial 3 | You are sitting in between two people. One of them starts to speak. Can you tell right away whether it is the person on your left or your right, without having to look? |
| 8 | Qualities 14 | Do you have to concentrate very much when listening to someone or something? |
| 9 | Qualities 13 | Can you easily judge another person's mood by the sound of their voice? |
| 10 | Qualities 11 | Do everyday sounds that you hear seem to have an artificial or unnatural quality? |
| 11 | Qualities 18 | Can you easily ignore other sounds when trying to listen to something? |
| 12 | Qualities 5 | Can you easily distinguish different pieces of music that you are familiar with? |

II. Results

A. Test-Retest Reliability

In spite of having additional participants with hearing loss, the test-retest reliability of the data in the current study was very close to that reported in example with normal-hearing participants. For example the mean absolute difference in $SRT_{50}$ thresholds in the standard QuickSIN condition (i.e., Babble) in the current study was 2.36 dB, compared to 2.3 dB reported by Brungart et al., 2014. The mean absolute difference in $SRT_{50}$ varied between 2.24 dB (Reverb) to 3.71 (AV and AV+N0Spi). The ranges for the mean absolute difference in $SRT_0$ and $SRT_{100}$ were 2.4-3.7 dB and 3.1-4.9 dB, respectively. Pearson correlation coefficient confirms that the two estimates for the three SRTs were significantly correlated ($p<1\times10-6$) in all conditions. Table IV lists the Pearson correlation coefficients. The two estimates were averaged for all subsequent analyses.

TABLE IV

Pearson correlation coefficient between two estimates of the three SRT values across all listeners. All correlations were statistically significant ($p < 1 \times 10_{-6}$).

| | Babble | AV | $N_0S_\pi$ | AV + $N_0S_\pi$ | Spatial | Reverb | TC + Rev | SSN |
|---|---|---|---|---|---|---|---|---|
| $SRT_0$ | 0.73 | 0.76 | 0.61 | 0.88 | 0.78 | 0.75 | 0.73 | 0.71 |
| $SRT_{50}$ | 0.57 | 0.47 | 0.83 | 0.71 | 0.65 | 0.84 | 0.73 | 0.68 |
| $SRT_{100}$ | 0.41 | 0.63 | 0.56 | 0.77 | 0.77 | 0.74 | 0.66 | 0.72 |

B. Effect of Participant Group and Listening Condition

FIG. 10 shows the average SRT50 values for the four listener groups in all listening conditions. As expected, thresholds for all subject groups significantly improved (p<0.001) due to visual input (AV versus Babble and AV+N0Sπ versus N0Sπ) and binaural release from masking (N0Sπ versus Babble and AV+N0Sπ versus AV). There was no significant improvement or degradation for any group in the SSN (p>0.16) condition, relative to the Babble condition. The three spatial conditions (Spatial, Rev, and TC+Rev) were not directly comparable to the babble condition because they had eight interfering talkers rather than four.
However, relative to the baseline Spatial condition, performance degraded significantly (p<0.001) due to Reverb and TC+Rev. In all the conditions, the speech-in-noise performance degraded (i.e., SRT50 increased) with moderate to severe hearing loss, but not with mild hearing loss. The average performances of H2 and H3 groups were worse than the control group (i.e., H1NH) in all listening conditions (p≤0.004 for H2 and p≤0.003 for H3), but the H1BN group did not show a significant deficit (p>0.075) in any condition. Compared with the standard QuickSIN condition (i.e., Babble), the speech-in-noise deficit was noticeably greater in N0Sπ, AV+N0Sπ, Reverb, and TC+Rev conditions. Analysis of variance revealed that the listener group had a significant main effect (p<0.001) on SRT50 in all listening conditions, but the effect was stronger than the standard condition [F(3,130)=18.405] only in N0Sπ [F(3,130)=20.087] and TC+Rev [F(3,130)=27.620] condition.

FIG. 11 shows cumulative distributions of SRT50 values in all listening conditions. In N0Sπ, Reverb, and TC+Rev conditions, some H3 listeners had SRT50 thresholds more than 20 dB higher than the average SRT50 for the control group (i.e., H1NH). Consistent with the analysis of variance results, the highest separation between cumulative distributions of H1NH and H2 or H3 group was observed in N0Sπ and TC+Rev Conditions. To quantify the separation among groups, SRT50 distribution of the H1NH group was compared with those of the other three groups in each listening condition using two-tailed student t tests, and the results are listed in Table V.

TABLE V

Results of two-tailed t-tests comparing distribution of $SRT_{50}$ values of the control group (i.e., H1NH) with that of the other three groups. Values in bold denote cases with statistically significant difference after Bonferroni correction (p < 0.0021).

| Group | Babble | AV | $N_0S_\pi$ | AV + $N_0S_\pi$ | Spatial | Reverb | TC + Rev | SSN |
|---|---|---|---|---|---|---|---|---|
| H1HL | −0.01 | 0.09 | −0.19 | 0.08 | −0.16 | 1.08 | 1.81 | 1.76 |
| H2 | 4.27 | 3.49 | 5.18 | 3.03 | 4.17 | 3.49 | 6.12 | 4.74 |
| H3 | 4.88 | 3.16 | 4.92 | 3.75 | 4.71 | 5.05 | 6.14 | 5.07 |

No statistically significant difference was observed between the H1NH and H1BN groups in any listening condition (p>0.75). H2 and H3 groups were significantly different (p<0.002) than the control group in all but one listening condition (AV+N0Sπ for H2 and AV for H3). But the highest separation, as indicated by the t statistics, was observed in the TC+Rev condition, followed by that in the N0Sπ condition. The Babble, Spatial, Reverb, and SSN conditions also show high degree of separation, with t statistics exceeding 4.5 for H3 and, in some cases, for H2 FIG. 12.

Another commonly used metric in clinical psychophysics for quantifying the performance of a patient is to compare it with the fifth percentile value of the control or the "normal" group (i.e., a performance level that 95% of the control group population achieves or exceeds). The fifth percentile level for the control group in each listening condition is denoted by the vertical dash-dotted line in FIG. 10. FIG. 11 shows that more than 58% of H3 subjects and more than 29% of H2 subjects performed worse than this level in Babble, N0Sπ, AV+N0Sπ, Reverb, TC+Rev, and SSN conditions.

C. Cross-Correlations

The eight listening conditions, although designed to test different aspects of speech-in-noise performance, could have redundancies due to common factors such as speech stimuli and the testing paradigm. Table VI shows Pearson correlation coefficients between the SNR50 values. Strong correlations (r>0.8) were observed between N0Sπ and AV+N0Sπ, and among Babble, Reverb, and TC+Rev conditions. The AV condition was not strongly correlated (r≤0.61) with any other condition, while Spatial and SSN conditions showed moderate correlations with each other as well as with other conditions (0.54≤r≤0.79).

TABLE VI

Cross-correlation coefficients among the eight listening conditions, calculated across all participants. All correlations were statistically significant ($r < 1 \times 10_{-7}$).

| | AV | $N_0S_\pi$ | AV + $N_0S_\pi$ | Spatial | Reverb | TC + Rev | SSN |
|---|---|---|---|---|---|---|---|
| Babble | 0.61 | 0.70 | 0.62 | 0.72 | 0.83 | 0.83 | 0.77 |
| AV | | 0.47 | 0.56 | 0.54 | 0.60 | 0.59 | 0.54 |
| $N_0S_\pi$ | | | 0.84 | 0.64 | 0.62 | 0.71 | 0.63 |
| AV + $N_0S_\pi$ | | | | 0.56 | 0.52 | 0.64 | 0.56 |
| Spatial | | | | | 0.79 | 0.75 | 0.69 |
| Reverb | | | | | | 0.81 | 0.76 |
| TC + Rev | | | | | | | 0.77 |

AV+N0Sπ conditions, where participants tended to underestimate their thresholds resulting in SRT50 values very close to SRT0 values, and the TC+Rev condition, where participants tended to overestimate their thresholds resulting in SRT50 values closer to their perceived SRT100. The results for the audiovisual conditions suggest that although listeners do not perceive the visual speech information to aid speech communication (possibly due to increased cognitive load required to process audiovisual stimuli), their speech-in-noise performance is improved by visual speech cues. On the other hand, the overestimated performance for the TC+Reverb condition indicates that listeners, irrespective of their hearing loss, feel that they can understand rapid speech, but in reality they make more errors than they think.

F. Perceived Hearing Difficulties

To test the ability of the speech-in-noise performance in various listening conditions to capture the speech-in-noise communication problems, the correlations between SRT values (both subjective and measured) and SSQ questionnaire ratings were calculated. FIG. 13 shows coefficient magnitudes for the correlations that were statistically significant after Bonferroni correction. SSQ questions 4, 7, 9, 11 and 12 had very weak or non-significant correlations with any SRT value in any condition. In general, SRT50 values were more highly correlated with SSQ ratings than the subjective thresholds. Only questions 2, 3, 4, and 10 had relatively strong correlations (r>0.35) with more than one condition. When compared by condition, only Babble, Reverb, TC+Rev and SSN conditions had correlations with r>0.35. TC+Rev and SSN were the only two conditions that yielded stronger correlations with SSQ questions than the standard QuickSIN condition (i.e., Babble). The AV condition was poorly correlated (r<0.3) with SSQ questions.

The only two conditions that were correlated with SSQ question six, which relates to the perceived location of sound source, were N0Sπ and AV+N0Sπ. This suggests that the two N0Sπ conditions could be potentially useful in evaluating the role of binaural integration ability in speech-in-noise communication. Question number eight, which pertains to attention and effort required while listening to speech in noise, correlated more with TC+Reverb condition (r>0.3) than any other condition. Therefore, one likely reason why all listeners found the TC+Rev condition to be the most challenging could be the higher cognitive load required for communicating in this condition.

IV. Discussion

In this study, a set of speech materials designed to evaluate speech perception in a variety of complex environments was used to examine how well listeners with different levels of hearing loss performed in each task. In designing the tests, it was hypothesized that some more complex speech environments might be more sensitive to the effects of hearing loss than the standard clinical version of the QuickSIN test, which presents a single talker monaurally or diotically in the presence of a four-talker babble in an anechoic space. Of the seven alternative listening conditions tested, two conditions stood out as being substantially more sensitive to the effect of hearing loss than the standard QuickSIN test1. The first was the TC+Reverb condition, which was highly correlated with the standard babble test but was substantially more sensitive to the effects of hearing loss. This suggests that the performance in the TC+Reverb condition is degraded by the same hearing deficits that interfere with performance in the standard QuickSIN task, but that these degradations are amplified by 290 the temporal distortions caused by the increased speech rate and simulated reverberation. Notably, the TC+Reverb condition was more correlated than any other condition with a survey question asking how much listeners needed to concentrate to understand speech, suggesting an interaction between cognitive effort and the extraction of fast speech from reverberant environments.

The second condition that appeared to be more sensitive to the effects of hearing loss than the standard Babble condition was the N0Sπ condition. However, in contrast to the TC+Reverb condition, the N0Sπ condition was very poorly correlated with performance in the standard babble condition. It was also one of the only two conditions (other being AV+N0Sπ) that were correlated with the SSQ question regarding the accuracy of sound localization. This suggests that it might be influenced by some aspect of binaural and spatial perception that is not addressed by the other conditions.

Overall, these results suggest that a hearing test regimen that combines the TC+Reverb task and the N0Sπ task might be an ideal combination for identifying hearing impaired individuals with speech-in-noise deficits. Interestingly, the TC+Reverb speech perception condition and N0Sπ tone detection (not speech perception) are also the two tests that other studies in our lab have found to be most sensitive to self-reported hearing deficits in blast-exposed individuals with normal or near-normal audiograms (Brungart et al, 2016).

It is also notable that the AV conditions of the experiment showed relatively little difference between the participants with different degrees of hearing loss. Comparing the AV and non-AV conditions with and without the N0Sπ manipulation, it appears that all listeners obtained approximately a 5 dB improvement in performance from the availability of visual cues. Also, in general, it seems that the AV cues tend to minimize the differences between hearing impaired and non-hearing impaired listeners, presumably 313 because performance is dominated more by differences in lip-reading skill than hearing loss in those conditions. Nevertheless, the AV conditions represent an important aspect of the everyday face-to-face communication.

Moreover, there may be some type of hearing loss or some hearing prostheses or hearing loss interventions that might be more sensitive to differences in visual cues, and the AV variants of the QuickSIN might be very useful in those situations.

A final note should be made about the usefulness of a technique based on method of adjustment to assess speech perception, rather than one based on objective speech intelligibility. In this experiment, listeners were fairly reliable at adjusting the level of masker to estimate the points of 100% and 0% speech intelligibility, and these subjective estimates were highly correlated with their objective SRT measurements ($p<1\times10^{-8}$). This suggests that method of adjustment can be a very useful tool for assessing within-subject, across-masker differences in speech intelligibility in cases where a very rapid estimate is needed or where limitations in the amount of available speech materials (for example, in the number of lists available in the QuickSIN) make it impractical to objectively test every condition. However, it does seem like these responses may also be influenced by other factors. For example, in this experiment the SRT100 condition was the only one correlated with the subjective question asking about the clarity of music. However, there were differences in these measures across listening conditions (especially in the AV and TC+Reverb conditions of this experiment), so care must be taken in using subjective measures to compare performance across different listening conditions.

REFERENCE

1) ANSI-S3.5 (1997), "American National Standard methods for 2 calculation of the speech intelligibility index," American National Standards Institute, Inc., reaffirmed by ANSI on April 2002.
2) Brungart, D. S., Kubli, L., Phatak, S., Kokx-Ryan, M. J., Bielski, L. M., Horvat, L., & Grant, K. W. (2016). "Functional hearing impairments in normal-hearing listeners with a history of deployment-related blast exposure," J. Acoust. Soc. Am., 140(4), 3152.
3) Brungart, D. S., Sheffield, B. M., and Kubli, L. R. (2014). "Development of a test battery for evaluating speech perception in complex listening environments," J. Acoust. Soc. Am., 136, 777-790.

4) Buss, E., Whittle, L. N., Grose, J. H., and Hall, J. W. (2009). "Masking release for words in amplitude-modulated noise as a function of modulation rate and task," J. Acoust. Soc. Am., 126, 269-280.
5) Cameron, S., Glyde, H., and Dillon, H. (2011). "Listening in Spatialized Noise-Sentences Test (LiSN-S): Normative and retest reliability data for adolescents and adults up to 60 years of age," J. Am. Acad. Audiol., 22, 697-709.
6) Dubno, J. R., Horwitz, A. R., and Ahlstrom, J. B. (2002). "Benefit of modulated maskers for speech recognition by younger and older adults with normal hearing," J. Acoust. Soc. Am., 111, 2897-2907.
7) Freyman, R. L., Balakrishnan, U, and Helfer, K. (2001). "Spatial release from informational masking in speech recognition," J. Acoust. Soc. Am., 109, 2112-2122.
8) Gatehouse, S., and Noble, W. (2004). "The Speech, Spatial and Qualities of hearing scale (SSQ)," Int. J. Audiol., 43, 85-99.
9) Garstecki, D. (1987). "Self-perceived hearing difficulty 365 in aging adults with acquired hearing loss," J. Acad. Rehabil. Audiol., 20, 49-60.
10) Gordon-Salant, S., and Fitzgibbons, P. J. (1993). "Temporal factors and speech recognition performance in young and elderly listeners," J. Sp. Hear. Res., 36, 1276-1285.
11) Hannula, S., Bloigu, R., Majamaa, K., Sorri, M., and Mäki-Torkko, E. (2011). "Self-reported hearing problems among older adults: prevalence and comparison to measured hearing impairment," J. Am. Acad. Audiol., 22(8), 550-559.
12) Institute of Electrical and Electronic Engineers (1969). "IEEE Recommended Practice for Speech Quality Measurements," IEEE, New York.
13) Jerger. J. (2011). "Why do people without hearing loss have hearing complaints?" J. Am. Acad. Audiol., 22(8), 490-490.
14) Killion, M. C., Niquette, P. A., Gudmundsen, G. I., Revit, L. J., and Banerjee, S. (2004). "Development of a quick speech-in-noise test for measuring signal-to-noise ratio loss in normal-hearing and hearing-impaired listeners," J. Acoust. Soc. Am., 116, 2395-2405.
15) Litovsky, R. Y. (2012). "Spatial release from masking," Acoustics Today 8(2), 18-23.
16) Miller, G. A., Heise, G. A., and Lichten, W. (1951). "The intelligibility of speech as a function of the context of the test materials," J. Exp. Psych., 41, 329-335.
17) Nilsson, M., Soli, S. D., and Sullivan, J. A. (1994). "Development of the hearing in noise test for the measurement of speech reception thresholds in quiet and in noise," J. Acoust. Soc. Am., 95,1085-1099.
18) Pienkowski, M. (2016). "On the etiology of hearing difficulties in noise despite clinically normal audiograms," Ear & Hearing, 97, 593-608.

What is claimed is:

1. A system for evaluating a listener's speech perception in complex listening environments, comprises:
   a) a test battery comprising a plurality of auditory simulation environments, wherein said auditory simulation environments comprises at least:
      i) a standard stimulus condition, which is a diotic presentation of a target speech in the presence of a masking noise;
      ii) a $N_0S_\pi$ or $N_0Spi$ stimulus condition, wherein is said target speech of said standard stimulus condition is phase shifted 180° in one ear; and
      iii) a time-compressed reverb stimulus condition,
         (1) wherein said standard stimulus condition is modified to simulate a spatial condition with the target speech presented in front of the listener, a first masking noise presented 90° to the left of the listener, and a second masking noise presented 90° to the right of the listener, each at a distance of 5 ft. in a simulated moderately reverberant room with a RT60 time of 0.25 s to produce a Reverb stimulus condition, and
         (2) wherein speaking rate of said target speech of Reverb stimulus condition is increased by 50%,
   b) transducers;
   c) a hearing test device capable of producing tones, speech and masking noise connected to the transducers;
   d) a computer connected to the hearing test device and storing said test battery, the test battery configured to cause the computer to
      i) present said plurality of simulated condition to said listener; and
      ii) generate a speech perception accuracy score based on the responses from the patient.

2. The system of claim 1, wherein said plurality of auditory simulation environments further comprises one or a combination of the following auditory simulation environments:
   a) an audiovisual stimulus condition (AV), wherein a video signal corresponding to said standard stimulus condition and said standard stimulus condition are simultaneously presented to said listener;
   b) an $AV+N_0S\pi$ stimulus condition, wherein a video signal of the corresponding to said standard stimulus condition and said $N_0S\pi$ stimulus condition is simultaneously presented to said listener;
   c) an spatial stimulus condition, wherein said which said standard stimulus condition is modified to simulate a spatial condition with the target speech presented in front of the listener, a first masking noise presented 90° to the left of the listener, and a second masking noise presented 90° to the right of the listener, each at a distance of 5 ft.;
   d) an Reverb stimulus condition, wherein said standard stimulus condition is modified as to be presented in a simulated moderate reverberated room with a RT time of 0.25 s; and
   e) an Speech-shaped noise (SSN) stimulus condition, which is a diotic presentation of said targeted speech and a continuous speech-spectrum shaped noise masker.

3. The system of claim 2, wherein said spatial stimulus condition is produced by applying head-related transfer functions (HRTFs) from Knowles Acoustic Manikin for Auditory Research (KEMAR) to said target speech and said first and second masking noises.

4. The system of claim 2, wherein said time-compressed reverb stimulus condition is produced by time compress the target speech signal of the standard stimulus condition using a PSOLA algorithm.

5. The system of claim 1, wherein said transducers are air conducting transducers or bone conduction transducers.

6. The system of claim 1, wherein said masking noise is a 4-talker babble.

7. A method for evaluating a listener's speech perception in complex listening environment, comprising:
   a) construct a test battery comprising a plurality of auditory simulation environments, wherein said auditory simulation environments include:

i) a standard stimulus condition, which is a diotic presentation of a target speech in the presence of a masking noise;
ii) a $N_0S_\pi$ or $N_0Spi$ stimulus condition, wherein is said target speech of said standard stimulus condition is phase shifted 180° in one ear; and
iii) a time-compressed reverb stimulus condition, wherein said standard stimulus condition is modified to simulate a spatial condition with the target speech presented in front of the listener, a first masking noise presented 90° to the left of the listener, and a second masking noise presented 90° to the right of the listener, each at a distance of 5 ft. in a simulated moderate reverberated room with a RT time of 0.25 s producing a Reverb stimulus condition, with speaking rate of said target speech of Reverb stimulus condition increased by 50%,
i) presenting said test battery to a listener;
ii) asking the listener to perform speech recognition task in each of said auditory stimulus conditions;
iii) estimating $SRT_{50}$ value of said listener; and
iv) identifying listener with speech-in-noise deficits based on $SRT_{50}$ value of said listener.

8. The method of claim 7, wherein said plurality of auditory simulation environments further comprises additional auditory simulation environments selected from the group consisting of auditory stimulus conditions comprising:
a) an audiovisual stimulus condition (AV), wherein a video signal corresponding to said standard stimulus condition and said standard stimulus condition are simultaneously presented to said listener;
b) an AV+$N_0S\pi$ stimulus condition, wherein a video signal of the corresponding to said standard stimulus condition and said $N_0S\pi$ stimulus condition is simultaneously presented to said listener;
c) an spatial stimulus condition, wherein said which said standard stimulus condition is modified to simulate a spatial condition with the target speech presented in front of the listener, a first masking noise presented 90° to the left of the listener, and a second masking noise presented 90° to the right of the listener, each at a distance of 5 ft.;
d) an Reverb stimulus condition, wherein said standard stimulus condition is modified as to be presented in a simulated moderate reverberated room with a RT time of 0.25 s; and
e) a Speech-shaped noise (SSN) stimulus condition, which is a diotic presentation of said targeted speech and a continuous speech-spectrum shaped noise masker.

9. The method of claim 8, wherein step (iv) of claim 7, further comprising
a) comparing said estimated $SRT_{50}$ value of said listener to a cutoff SRT; and
b) identifying listener with speech-in-noise deficits based on $SRT_{50}$ value of said listener greater than the cutoff SRT.

10. A method for testing hearing prosthesis or hearing protection device,
a) construct a test battery comprising a plurality of auditory simulation environments, wherein said auditory simulation environments at least include:
i) a standard stimulus condition, which is a diotic presentation of a target speech in the presence of a modified masking noise;
ii) a $N_0S_\pi$ or $N_0Spi$ stimulus condition, wherein is said target speech of said standard stimulus condition is phase shifted 180° in one ear; and
iii) a time-compressed reverb stimulus condition, which said standard stimulus condition is modified to simulate a spatial condition with the target speech presented in front of the listener, a first masking noise presented 90° to the left of the listener, and a second masking noise presented 90° to the right of the listener, each at a distance of 5 ft. in a simulated moderate reverberated room with a RT time of 0.25 s producing a Reverb stimulus condition, wherein speaking rate of said target speech of Reverb stimulus condition is increased by 50%,
v) presenting said test battery to a listener;
vi) asking the listener to perform speech recognition tasks in each of said auditory stimulus conditions;
vii) estimating SRT50 value of said listener; and
viii) determining the effect of said hearing prosthesis or hearing protection device on said listener's speech perception.

11. The method of claim 10, wherein step (viii) of claim 10, further comprising
a) comparing said estimated $SRT_{50}$ value of said listener to a cutoff SRT; and
b) finding said hearing prosthesis or hearing protection device effective if said $SRT_{50}$ value of said is greater than the cutoff SRT.

* * * * *